United States Patent [19]
Scribner et al.

[11] Patent Number: 5,830,125
[45] Date of Patent: Nov. 3, 1998

[54] CATHETER INTRODUCER WITH SUTURE CAPABILITY

[75] Inventors: Robert M. Scribner, Boulder, Colo.; Kevin F. Browne, Lakeland, Fla.

[73] Assignee: Scribner-Browne Medical Design Incorporated, Los Altos, Calif.

[21] Appl. No.: 407,886

[22] Filed: Mar. 21, 1995

Related U.S. Application Data

[63] Continuation-in-part of Ser. No. 105,411, Aug. 12, 1993, abandoned.

[51] Int. Cl.$^6$ .................................................... A61B 17/04
[52] U.S. Cl. ........................... 606/139; 606/144; 606/148; 604/96; 604/164; 604/158
[58] Field of Search ..................................... 606/139, 144, 606/148, 213; 604/96, 164, 158

[56] References Cited

U.S. PATENT DOCUMENTS

| | | | |
|---|---|---|---|
| 4,168,073 | 9/1979 | LaRue | 279/2 R |
| 4,437,465 | 3/1984 | Nomoto et al. | 128/340 |
| 4,493,323 | 1/1985 | Albright et al. | 128/340 |
| 4,526,173 | 7/1985 | Sheehan | 128/335 |
| 4,587,969 | 5/1986 | Gillis | 128/334 R |
| 4,602,635 | 7/1986 | Mulhollan et al. | 606/144 |
| 4,836,205 | 6/1989 | Barrett | 128/340 |
| 4,852,568 | 8/1989 | Kensey | 128/325 |
| 4,898,155 | 2/1990 | Ovil et al. | 606/144 |
| 4,957,498 | 9/1990 | Caspari et al. | 606/146 |
| 4,995,868 | 2/1991 | Brazier | 604/105 |
| 5,009,663 | 4/1991 | Broome | 606/232 |
| 5,021,059 | 6/1991 | Kensey et al. | 606/213 |
| 5,037,433 | 8/1991 | Wilk et al. | 606/144 |
| 5,061,274 | 10/1991 | Kensey | 606/213 |
| 5,066,288 | 11/1991 | Deniega et al. | 604/274 |
| 5,073,166 | 12/1991 | Parks et al. | 609/93 |
| 5,122,122 | 6/1992 | Allgood | 604/174 |
| 5,176,648 | 1/1993 | Holmes et al. | 604/164 |
| 5,192,300 | 3/1993 | Fowler | 606/213 |
| 5,192,302 | 3/1993 | Kensey et al. | 606/213 |
| 5,217,451 | 6/1993 | Freitas | 606/1 |
| 5,222,508 | 6/1993 | Contarini | 128/898 |
| 5,279,551 | 1/1994 | James | 604/144 |
| 5,281,234 | 1/1994 | Wilk et al. | 606/144 |
| 5,304,184 | 4/1994 | Hathaway et al. | 606/144 |
| 5,439,469 | 8/1995 | Heaven et al. | 606/144 |
| 5,496,332 | 3/1996 | Sierra et al. | 606/139 |
| 5,507,775 | 4/1996 | Gresl et al. | 606/139 |

FOREIGN PATENT DOCUMENTS

| | | | |
|---|---|---|---|
| 1644915 | 4/1991 | U.S.S.R. | 606/222 |
| PCT/US93/ 11864 | 12/1993 | WIPO . | |

OTHER PUBLICATIONS

Ragnarrson, et al., "Microvascular Anastomoses in Irradiated Vessels: A Comparison Between the Unilink System and Sutures," *Plastic and Reconstructive Surgery*, Mar. 1990, pp. 412–418.

Nakayama, et al., "A Simple new Apparatus for Small Vessel Anastomosis (Free Autograft of the Sigmoid Included)," *Surgery*, vol. 52, No. 6, Dec. 1962, pp. 918–931.

Goetz, et al., "A Nonsuture Method Employing Tantalum Rings," *Internal Mammary–Coronary Artery Anastomosis*, vol. 41, No. 3, Mar. 1961, pp. 378–381.

*Primary Examiner*—Gary Jackson
*Attorney, Agent, or Firm*—Sheridan Ross, P.C.

[57] ABSTRACT

An assembly is provided for suturing an incision in a tissue wall of a patient with a suture material. The assembly comprises a carrier member, a distal member interconnected to the carrier member, and a guide member positioned about and moveable along the carrier member. The guide member guides an access device through the tissue wall at two or more different locations adjacent to the incision in the tissue wall such that suture material is threadable through and into the tissue wall at a first location and through and back out of the tissue wall at a second location.

64 Claims, 19 Drawing Sheets

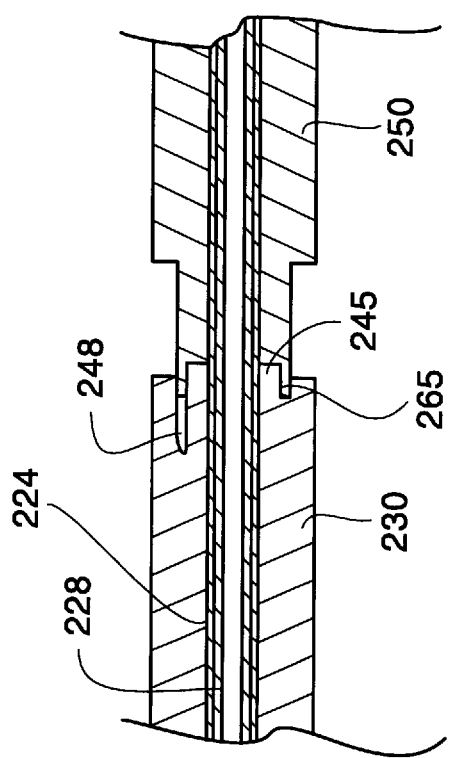

CATHETER INTRODUCER WITH SUTURE CAPABILITY

RELATED APPLICATIONS

This patent application is a continuation in part of co-pending U.S. patent application Ser. No. 08/105,411, filed on Aug. 12, 1993, now abandoned, the entire disclosure of which is incorporated by reference herein.

FIELD OF THE INVENTION

The present invention relates to medical devices for closing incisions and, more particularly, to a catheter introducer capable of assisting in threading a suture material through a tissue wall surrounding an incision and withdrawing the suture material back through the incision.

BACKGROUND OF THE INVENTION

Catheter introducers are routinely used for access to the arterial system, providing a means of entry into the interior of an artery while inhibiting blood loss during catheter procedures. For example, catheter introducers are used for introduction of balloon angioplasty catheters into the femoral artery of a patient for access to the coronary arteries via the ascending and descending aorta to perform percutaneous transluminal coronary angioplasty.

Catheter introducers typically comprise an elongated tubular member open at both ends, a tubular dilator slidably positionable within the tubular member, and a guidewire slidably positionable within the dilator. Catheter introducers can be introduced into an artery utilizing a standard insertion procedure, such as the Seldinger technique. In the Seldinger technique, the artery wall is pierced by a stylet and cannula, the stylet is removed, the guidewire is inserted through the cannula, and the cannula is removed from the artery. The introducer, comprising the elongated tubular member and dilator assembly, is then introduced over the guidewire until the distal tip of the elongated tubular member is positioned within the artery. The dilator and guidewire are subsequently removed to allow standard catheter procedures to be performed (e.g., coronary angiography or percutaneous transluminal coronary angioplasty).

On completion of the catheter procedure, the elongated tubular member is removed from the artery, leaving an arterial incision (i.e., in the wall of the artery) below the skin line. This incision can be the source of blood loss, hematoma and other complications. Closure of such incisions by standard suturing procedures (i.e., needle and thread) is complicated by the depth of the arterial incision below the skin line. Consequently, the current practice is to stop bleeding by the application of pressure to the incision, either manually or by a clamping device, or by the insertion of a plugging member into the incision to inhibit blood loss therefrom. Such current techniques can be costly due to the required medical staff time to perform the procedures, and can result in prolonged recovery times and patient discomfort.

SUMMARY OF THE INVENTION

It is a primary object of the present invention to provide an apparatus and method for effectively suturing an incision in a tissue wall of a patient without the need for invasive surgery.

It is a further object of the present invention to provide an invasive medical device in which suture material can be threaded through a tissue wall in a patient and into an interior of the device while the device remains in the incision.

In one aspect, the present invention is embodied in an assembly particularly adapted to facilitate threading of a suture material through a tissue wall of a patient and withdrawing the suture material back through an incision which was created for performing a medical procedure. The assembly includes a first elongated member having a hollow portion and at least one opening through a sidewall adjacent the hollow portion. The first elongated member is positionable through the incision with the opening being inside the tissue wall of the patient. Means for inserting a suture material through the tissue wall and through the opening of the first elongated member is provided, whereby the suture material may subsequently be withdrawn back through the incision. When multiple sutures are threaded in this manner on opposing sides of the incision, the sutures can be tied together by known techniques to effectively close the incision.

The means for inserting may preferably include a second elongated member positioned about the first elongated member and having an access hole therethrough. The second elongated member may include an expandable portion selectably expandable from a retracted diameter to an expanded diameter larger than the retracted diameter to create a cavity between the first and second elongated members. Preferably, distal movement of a second proximal end of the second elongated member relative to a first proximal end of the first elongated member results in expansion of the expandable portion. More preferably, a second distal end of the second elongated member is secured to a first distal end of the first elongated member and the second proximal end is slidable relative to the first proximal end. The second elongated member may further include longitudinal slits through the expandable portion, whereby distal movement of the second proximal end relative to the first proximal end results in expansion of the expandable portion to form wing portions defining the cavity.

The cavity is preferably positioned over the opening of the first elongated member and in alignment with the access hole, such that an access path for the suture material (i.e., from the exterior of the assembly to the hollow portion in the first elongated member) is formed. For example, the means for inserting the suture material may insert the suture material through the tissue wall, access hole, cavity, and opening to position at least a portion of the suture material in the hollow portion of the first elongated member. In addition, to provide a means for securing the suture material within the assembly, the access hole may be misaligned with the openings when the second elongated member is the retracted position.

The means for inserting may further comprise at least one needle insertable through the tissue wall and through the access hole in the second elongated member. Such a needle may facilitate introduction of the suture material into the hollow portion (e.g., by having the suture material detachably secured to the needle during insertion of the needle through the tissue wall and access hole). Preferably, the needle is hollow and thereby provides a pathway through which the suture material may be introduced. Introduction of the suture material through the hollow needle may be facilitated by utilizing a suture material having a guide tip (e.g., a flexible guidewire tip) integral therewith and further by utilizing a cannula for pushing the guide tip (including the suture material) through the hollow needle and into the hollow portion of the first elongated member.

When used with an assembly having first and second elongated members forming a cavity, the hollow needle may be inserted through the tissue wall of the patient and through the access hole to position a tip of the hollow needle in the cavity formed by the wing portion. When the suture material (e.g., having a guide tip) is inserted through the hollow needle, the wing portion acts to deflect the suture material (e.g., the guide tip) into the opening.

The assembly may further comprise a third member positioned about the second elongated member and having at least one lumen extending therethrough for receiving and guiding the needle toward the access hole. The lumen is preferably positioned parallel to the first and second elongated members and in alignment with the access hole when the expandable portion is expanded. The third member may also be movable axially relative to the second elongated member in order to accommodate varying depths of the tissue wall below the skin line.

To withdraw the suture material back through the incision, the assembly may further comprise a means for engaging the suture material within the hollow portion, whereby removal of the means for engaging from the first elongated member will result in withdrawal of the suture material back through the incision. Such means may, for example, include an engaging member positionable within the hollow portion and having a mechanical grip (e.g., a clamp, snare or other device), adhesive layer, or magnet (e.g., if the guide tip is metallic) on one end thereof for engaging the suture material (e.g., guide tip).

Alternatively, the suture material may be withdrawn from the incision by securing the suture material within the hollow portion of the first elongated member and removing the first elongated member from the incision. It may be necessary to provide a separate means for securing in order to prevent the suture material from sliding out of the hollow portion during removal of the first elongated member. Such means may comprise a fourth member slidably positionable within the hollow portion of the first elongated member. More specifically, after the suture material is properly positioned within the hollow portion, the fourth member may be advanced toward the opening to restrict the suture material (e.g., the guide tip) between the fourth member and the sidewall of the first elongated member to thereby prevent the suture material from sliding out of the hollow portion when the first elongated member is removed from the incision. Alternatively, the means for securing may comprise an expandable member positionable within the hollow portion and expandable to secure the suture material (e.g., the guide tip) within the hollow portion. The fourth member (and/or expandable member) may also act as a vessel dilator on introduction of the assembly into the artery.

In one embodiment, the invention comprises an arterial catheter introducer comprising a hollow first tube for introducing a catheter into an artery, a dilator for facilitating insertion of the first tube into an arterial incision, and a guidewire for guiding the dilator and first tube into the incision. Such an introducer may be used to perform transluminal coronary angioplasty procedures prior to closure of the incision utilizing the features of the present invention. The first tube is provided with two openings positioned on opposing sides thereof near the first distal end. A second tube is positioned around the first tube and is secured to the first tube at the distal ends thereof, but is slidable relative to the first tube at the proximal ends thereof.

The second tube is further provided with four longitudinal slits defining an expandable portion proximal to the first distal ends. Upon distal movement of the second proximal end relative to the first proximal end, the material between the four longitudinal slits expands to define four wing portions, two of which are aligned with the openings in the first tube. The expandable portion further includes two access holes on proximal portions of the two aligned wing portions. A third member is positioned around the second tube proximal to the expandable portion and defines lumens on opposing sides of the second tube approximately parallel to the first and second tubes. The lumens are designed to slidably receive and guide the hollow needles toward the access holes in the expandable portion when the expandable portion is expanded.

In another aspect, the present invention is embodied in an assembly particularly adapted to facilitate threading of a suture material into a tissue wall at a first location adjacent to an incision and back out of the tissue wall at a second location adjacent to the incision. The assembly includes a carrier member, a distal member interconnected to the carrier member and positionable through an incision at least partially inside the tissue wall, and a guide member positioned about and moveable along the carrier member for guiding suture access means through the tissue wall at two or more different locations adjacent to the incision. In this embodiment, the access means comprises two or more needles.

In a corresponding embodiment, the guide member is rotatable about the carrier member and the access means includes a single needle for defining a first opening through the tissue wall at the first location and, upon rotation of the guide member about the carrier member, for defining a second opening through the tissue wall at the second location. The guide member may include a first lumen axially extending therethrough for receiving and guiding the access means through the tissue wall at the first and second locations and a second lumen axially extending therethrough for receiving the suture material as the suture material exits from one of the first and second openings in the tissue wall.

In this embodiment, the distal member may include a recess therein for guiding the suture material and, more specifically, the guide tip connected thereto, about the interior of the distal member to reverse the path of the guide tip. Such a recess is generally arcuate and extends between the proximal end of the distal member and is open to the proximal end to facilitate suturing of the incision.

The apparatus may also include an aligning means to ensure proper alignment of the access means at two or more predetermined positions, which substantially correspond with the first and second locations of the tissue wall. The aligning means may comprise a visual indication of angular rotation of the guide member relative to the distal member, and more preferably, may comprise slots and associated fins or tabs on the proximal and distal ends of the distal and guide members, respectively.

As will be appreciated, because suture material can be threaded through a tissue wall below the skin layer while the medical device is in the incision, the present invention allows suturing of subepidermal incisions without excessive fluid loss therefrom and without the need for invasive surgical procedures. The present invention allows the position and sealing of the suture to be assessed prior to removal of the device from the incision. The invention also allows for the placement of multiple sutures about the incision site. Furthermore, the suturing which can be accomplished utilizing the present invention substantially reduces the need to apply pressure to the incision or to insert a plugging member therein to remedy blood loss, hematoma and other complications.

These and other features, advantages and objects of the present invention will be further understood and appreciated by those skilled in the art by reference to the following written specification, claims and appended drawing.

BRIEF DESCRIPTION OF THE DRAWINGS

FIG. 10 is a section view of another embodiment of the apparatus.

DETAILED DESCRIPTION

FIGS. 1–4 illustrate an arterial catheter introducer embodying the features of the present invention. Although this embodiment of the present invention will be described with reference to a catheter introducer, it should be appreciated that the present invention is also applicable to other invasive medical devices wherein it is desirable to close an incision left by the device. For example, the present invention could be used with a trocar assembly used in laparoscopic surgery to close an incision created by the trocar assembly or with a gastrostomy feeding tube to close an incision created by the feeding tube.

For ease of description, in the discussion of the apparatus 10, the term "distal" refers to the direction toward the patient (e.g., the direction toward the top of the page in FIGS. 2A–2F). Correspondingly, the term "proximal" refers to the direction away from the patient (e.g., the direction toward the bottom of the page in FIGS. 2A–2F).

Figure 1:
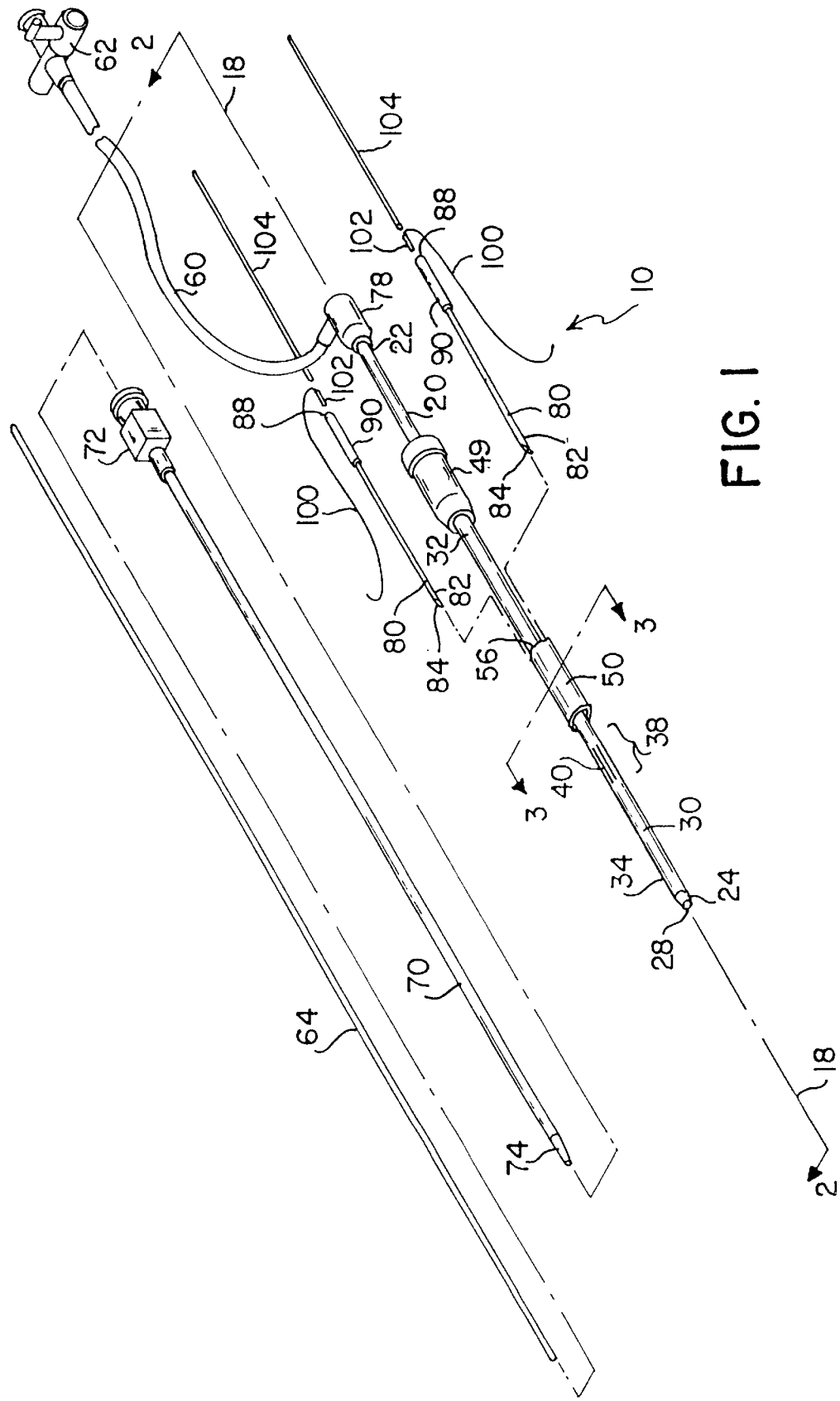
FIG. 1 is an exploded assembly view of an apparatus embodying the present invention.

Referring to FIG. 1, the apparatus 10 generally comprises a first tube 20 for introducing a catheter (not shown) into an artery, a second tube 30 positioned around the exterior of the first tube 20, and a positioning member 50 positioned around the exterior of the second tube 30. A dilator 70 and guidewire 64 are provided for facilitating insertion of the first and second tubes 20, 30 into an artery and for achieving and maintaining access to the artery during the suturing procedure of the present invention. A sidearm tube 60 with a stopcock 62 extends from a proximal end 22 of the first tube 20 for fluid withdrawal or medication injection. The apparatus 10 further includes hollow needles 80, guide tips 102 attached to suture material 100, and hollow cannulas 104 for introducing the suture material 100 through the artery wall 12 and into the interior of the first tube 20.

Referring to FIG. 2A–2E, the first tube 20 of the present embodiment is an elongated, hollow cylindrical member open at both a first proximal end 22 and a first distal end 24 and having a central longitudinal axis 18. Because the present embodiment will be used as an arterial catheter introducer, the interior 28 of the first tube 20 should have a diameter large enough for insertion of a catheter appropriately sized for the specific application. For example, interior diameters of such catheter introducers are typically in the range of 0.065 inches to 0.117 inches (5 French to 9 French) and, for femoral artery applications, are preferably at least about 0.079 inches (6 French).

The first tube 20 is provided with two openings 26 positioned on opposing sides thereof (i.e., 180° from each other) near the first distal end 24. These openings 26 allow access to the interior 28 of the first tube 20 by the suture material 100, as will be explained herein in more detail. Such openings 26 are generally oblong-shaped with the longer dimension being aligned with the longitudinal axis 18. Such oblong shape facilitates insertion of the cylindrically-shaped guide tips 102 therein, as will be described below in more detail. For the present embodiment, the openings 26 have dimensions of approximately 0.060 inches by 0.250 inches. The first tube 20 is preferably made from a polymer-based material such as polyolefin, polytetraflouroethylene, polyurethane and, most preferably, polyethylene.

Means for inserting the suture material 100 is provided for getting the suture material 100 inside the first tube 20. In the disclosed embodiment, such means for inserting includes a second tube 30 positioned over the first tube 20 and generally concentric therewith (i.e., the second tube 30 has the same central longitudinal axis 18 as the first tube 20). Similar to the first tube 20, the second tube 30 is an elongated, hollow cylindrical member with an interior diameter slightly greater than the exterior diameter of the first tube 20 such that when the second tube 30 is positioned over the first tube 20 there is a slidable fit therebetween. For example, in the present embodiment, the interior diameter of the second tube 30 is about 0.134 inches and the exterior diameter of the first tube 20 is about 0.130 inches. A second distal end 34 of the second tube 30 is secured to the first distal end 24 of the first tube 20 at a secured portion 36 located distal to the openings 26 in the first tube 20. Correspondingly, the remainder of the second tube 30 (proximal to the secured portion 36) is slidable relative to the first tube 20.

Figure 2A:
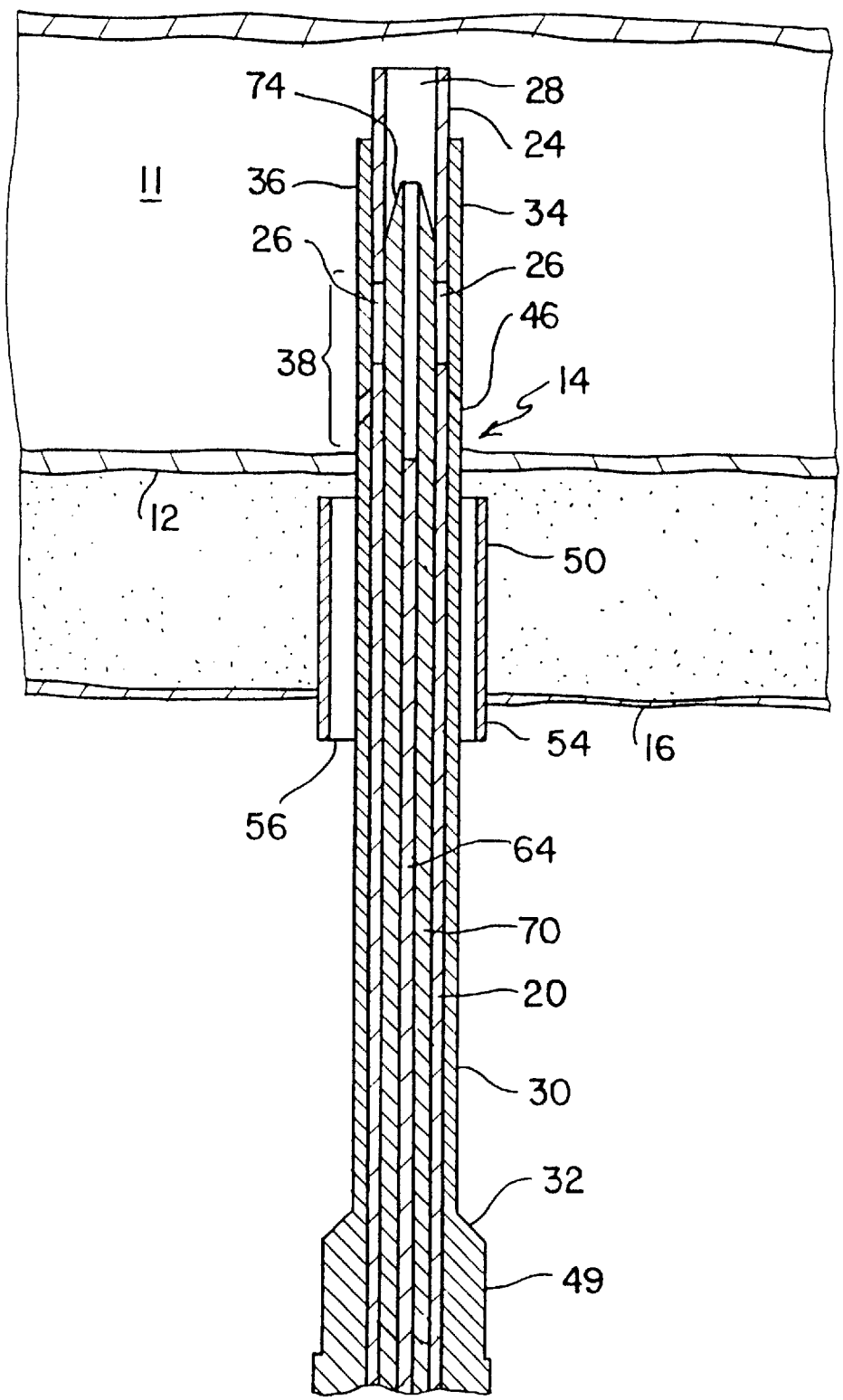
FIG. 2A is a longitudinal section taken along line 2—2 in FIG. 1 with the apparatus inserted into an incision in an artery wall.
Figure 2B:
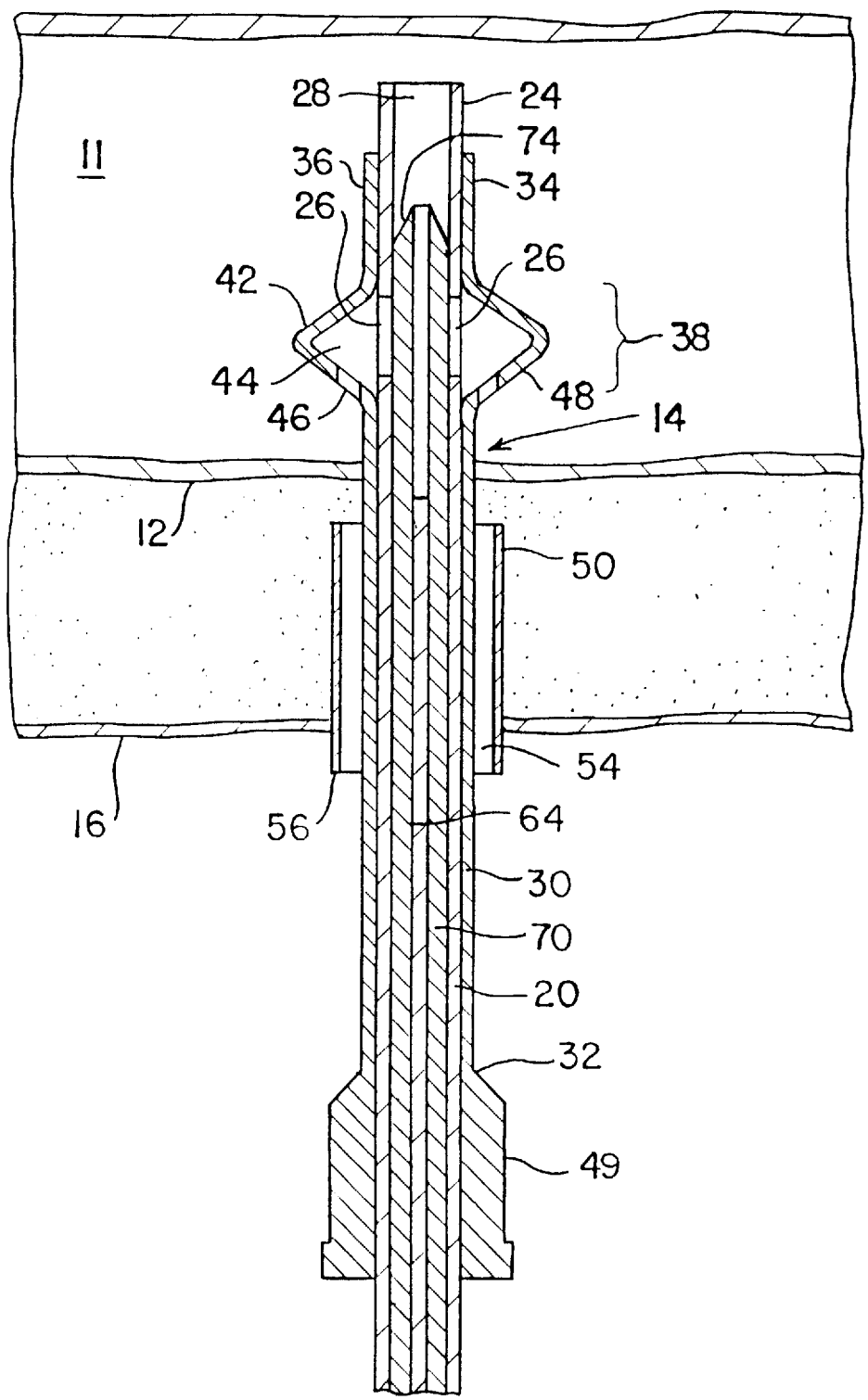
FIG. 2B is the section view of FIG. 2A with the apparatus in the expanded position.

Four longitudinal slits 40 are provided to define an expandable portion 38 of the second tube 30 proximal to the secured portion 36 and aligned with the openings 26 in the first tube 20. The slits 40 are designed such that distal sliding movement of the second proximal end 32 relative to the first tube 20 in a telescoping manner results in the expandable portion 38 of the second tube 30 moving radially outward to form four wings 42, as shown in FIG. 2B. Such radial outward movement of the expandable portion 38 effectively expands the expandable portion 38 from a retracted diameter, shown in FIG. 2A, to an expanded diameter, shown in FIG. 2B, larger than the retracted diameter. The extent to which the expandable portion 38 increases in diameter is proportional to the length of the longitudinal slits 40. That is, the longer the slits 40, the greater the increase in diameter of the expandable portion 38. In the present embodiment, the slits 40 are about 0.250 inches long, resulting in expansion of the expandable portion 38 from about 0.150 inches to about 0.275 inches.

The provision of a second tube 30 having an expandable portion 38 serves several useful functions. For example, the expandable portion 38 provides a back support behind the artery wall 12 to facilitate piercing of the artery wall 12 by the hollow needles 80, as described in more detail below. Also, the expandable portion 38 creates a cavity 44 over the openings 26 to deflect the guide tips 102 from the hollow needles 80 toward the openings 26, as described below. In addition, when in the expanded condition, the expandable portion 38 inhibits inadvertent withdrawal of the apparatus 10 from the incision 14 during suturing procedures. The ability to expand and retract is especially preferable because it allows the apparatus 10 to be inserted and withdrawn from the incision 14 in the retracted condition, thereby reducing the need to undesirably enlarge the incision 14.

Two of the wings 42 are aligned with the openings 26 in the first tube 20 such that, when they are expanded, they define generally triangular-shaped cavities 44 over the openings 26 and into which the suture material 100 will be introduced, as described below. It should be appreciated that, by proper material selection, the expandable portion 38 could expand into a bulge, similar to a rivet, rather than wings 42, without the need for the longitudinal slits 40. Similar to the first tube 20, the second tube 30 preferably comprises a polymer-based material such as polyolefin, polytetraflouroethylene, polyurethane and, most preferably, polyethylene.

Access holes 46 are provided in the proximal portion 48 of the two aligned wings 42 to facilitate access to the cavities 44 by hollow needles 80, as described below. Preferably, the access holes 46 are aligned parallel to the longitudinal axis 18 when the expandable portion 38 of the second tube 30 is fully expanded to form the wings 42. Furthermore, it is preferable that the access holes 46 are misaligned with the openings 26 in the first tube 20 when the expandable portion is retracted. That is, the access holes 46 are proximal to the openings 26 in the retracted position and do not overlap therewith. Such positioning of the access holes 46 relative to the openings 26 effectively restricts the suture material 100 (e.g., the guide tip 102) when the wings 42 are retracted, thereby retaining the suture material 100 (e.g., the guide tip 102) in the interior 28 of the first tube 20 when the apparatus 10 is being withdrawn from the incision 14.

A hemostasis valve contained within a fitting 49 is secured to the second proximal end 32 in order to inhibit blood leakage between the first tube 20 and the second tube 30. The fitting 49 also serves as a grip which the user of the device can readily hold to provide distal movement of the second proximal end 32 relative to the first proximal end 22 to expand the expandable portion 38, as described above.

The means for inserting in the disclosed embodiment further includes a positioning member 50 positioned about the second tube 30. The positioning member 50 is an elongated hollow member having an oblong cross-section. A central portion 52 of the cross-section follows a generally cylindrical shape with an inner diameter approximately equal to the outer diameter of the second tube 30 (e.g., about 0.150 inches in the present embodiment). The central portion 52 of the positioning member 50 is secured to the second tube 30 at a location proximal to the expandable portion 38 of the second tube 30. Alternatively, the positioning member 50 could be slidable axially relative to the second tube 30 to account for different depths of the arterial incision 14 relative to the skin line 16 of the patient.

Figure 3A:
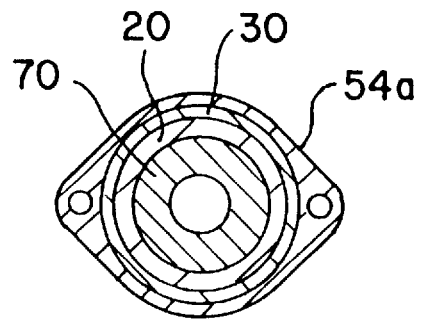
FIG. 3A is the section view of FIG. 3 showing an alternative embodiment of the positioning member.
Figure 3:
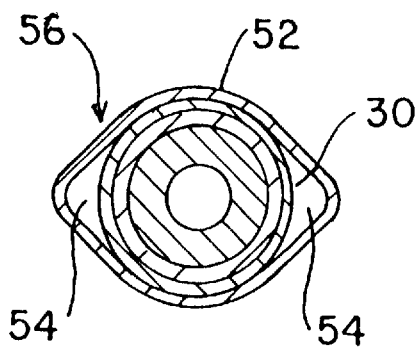
FIG. 3 is a section view taken along line 3—3 in FIG. 1.
Figure 4:
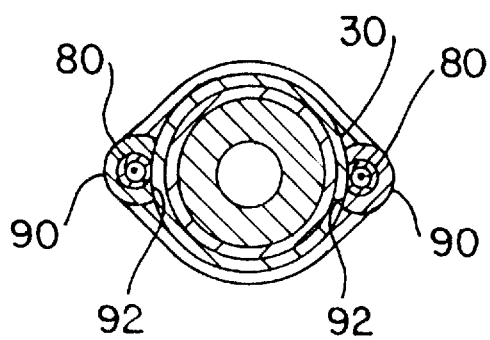
FIG. 4 is a section view taken along line 4—4 in FIG. 2C showing details of the contoured stop members.

As shown in FIGS. 3 and 4, the oblong shape of the positioning member 50 defines lumens 54 on opposing sides of the second tube 30 (i.e., 180° from each other) travelling the length of the positioning member 50. The lumens 54 extend approximately parallel to the longitudinal axis 18 and are in alignment with the access holes 46 in the wings 42 of the second tube 30 when the wings 42 are fully expanded. The lumens 54 are sized to slidably receive the hollow needles 80 therein and function to align the hollow needles 80 relative to the access holes 46. Similar to the first and second tubes 20, 30, the positioning member 50 preferably comprises a polymer-based material such as polyolefin, polytetraflouroethylene, polyurethane and, most preferably, polyethylene.

Alternatively, it should be appreciated that the lumens 54 could be separate, cylindrically-shaped passageways 54a formed through the positioning member 50 on opposing sides thereof, as shown in FIG. 3A. In such an arrangement, the diameter of the passageways 54a may be slightly larger than the diameter of the hollow needles 80 to facilitate sliding interaction therebetween. Similar to the arrangement shown in FIG. 3, the passageways 54a extend approximately parallel to the longitudinal axis 18 and are in alignment with the access holes 46 in the wings 42 of the second tube 30 when the wings 42 are fully expanded. As with the lumens 54, the passageways 54a function to align the hollow needles 80 relative to the access holes 46.

The dilator 70 is an elongated, hollow cylindrical member having an outer diameter slightly smaller than the inner diameter of the first tube 20 (e.g., about 0.077 inches in the present embodiment) and an inner diameter slightly larger than the introducer guidewire 64 (e.g., about 0.040 inches in the present embodiment). The dilator 70 is slidably positionable over the introducer guidewire 64 and within the interior 28 of the first tube 20. The proximal end 72 of the dilator 70 is enlarged and extends beyond the first proximal end 22 so that the dilator 70 can be gripped by the user and selectively moved to different positions within the first tube 20. The distal end 74 of the dilator 70 is preferably conically shaped to facilitate insertion of the apparatus 10 into an incision 14 in an artery wall 12. A hemostasis valve contained within a housing 78 is secured to the first proximal end 22 to provide a seal between the dilator 70 and the first tube 20 to inhibit blood leakage therebetween. In addition to performing the functions of a standard dilator 70 (i.e., facilitating insertion of the introducer into the incision 14), the dilator 70 of the present invention also functions as a means for retaining the suture material 100 (e.g., the guide tips 102) within the first tube 20 as the apparatus 10 is being withdrawn from the incision 14, as described below.

In the alternative, it should be appreciated that the dilator 70 could comprise any means for securing the suture material 100 within the first tube 28. For example, the dilator 70 could comprise an inflatable member selectably positionable within the interior 28 of the first tube 20, such that the inflatable member can be appropriately inflated/expanded to secure the suture material 100 between the inflatable member and the interior 28 of the first tube 20.

Figure 2C:
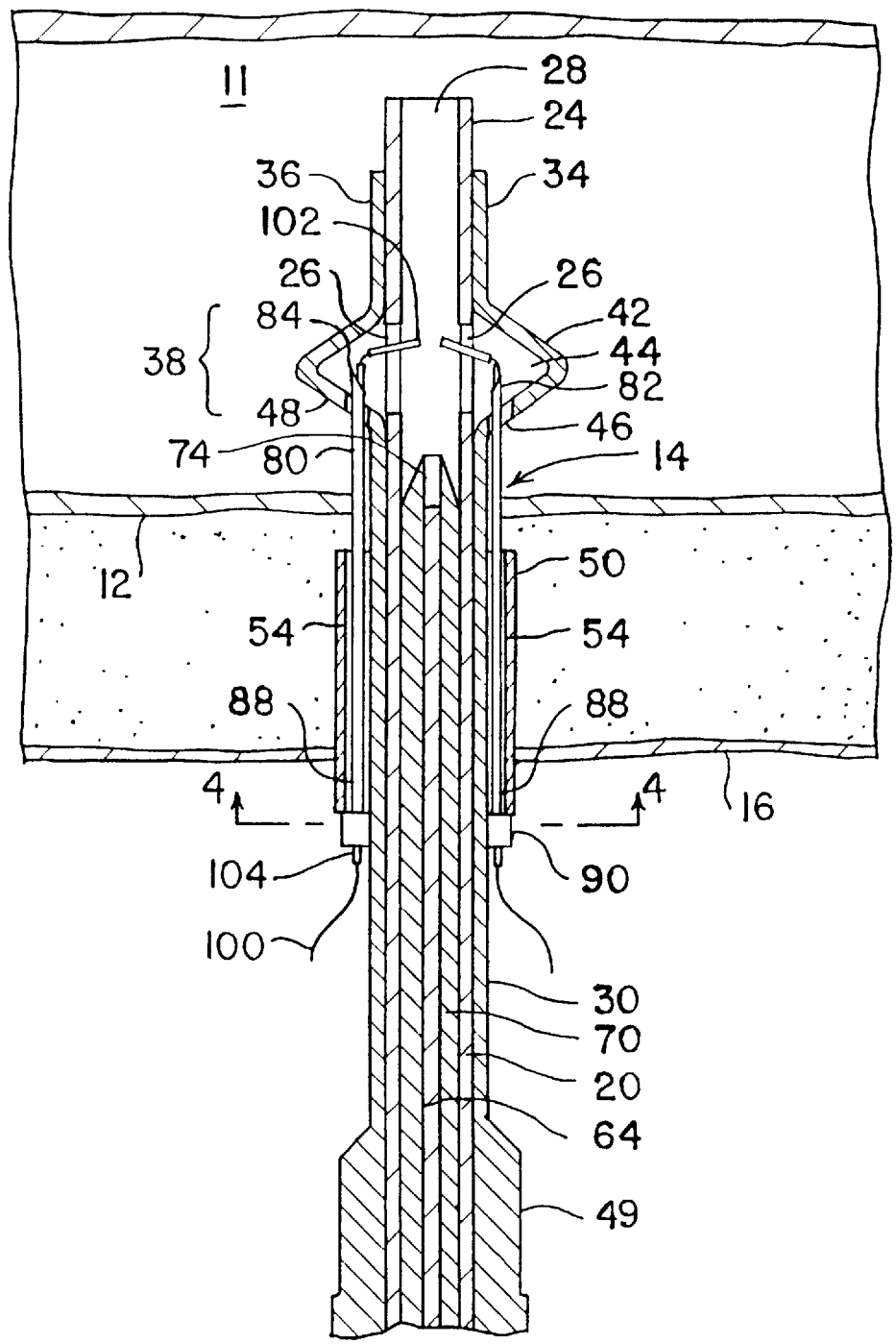
FIG. 2C is the side view of FIG. 2A showing the suture material inserted into the artery.

Referring now to FIG. 2C, the means for inserting in the disclosed embodiment further includes hollow needles 80 which are utilized to provide access to the cavities 44 formed by the wings 42. As with most medical needles, the distal tips 82 of the hollow needles 80 are beveled to facilitate piercing of the needles through the artery wall 12. The outer diameter of the hollow needles 80 is designed such that the hollow needles 80 can be slidably inserted through the lumens 54 in the positioning member 50 toward the expanded wings 42 of the second tube 30. Because, as noted above, the access holes 46 in the wings 42 are aligned with the lumens 54 in the positioning member 50, further insertion of the hollow needles 80 through the lumens 54 will result in the distal tips 82 of the hollow needles 80 passing through the access holes 46 of the wings 42 and entering the cavities 44.

In use, the apparatus 10 will be positioned in an incision 14 with an artery wall 12 between the positioning member 50 and the expandable portion 38 of the second tube 30. Consequently, the hollow needles 80 will pierce the artery wall 12 as they are being inserted through the lumens 54 toward the access holes 46 in the wings 42. In this regard, it is desirable to rotationally orient the hollow needles 80 such that the beveled face 84 of both distal tips 82 face toward the central longitudinal axis 18. Such an orientation performs two functions. First, it causes the hollow needles 80 to initiate piercing of the artery wall 12 further away from the central longitudinal axis 18, thus providing greater arterial wall 12 to be engaged between the suture material 100 and the incision 14, resulting in less chance for the artery wall 12 to tear when the suture material 100 is tied. Second, orienting the hollow needles 80 in such a position provides a more direct path for the guide tip 102 to follow when entering the interior 28 of the first tube 20, as described below.

In order to insure proper rotational orientation of the hollow needles 80 within the positioning member 50, yet allow the hollow needles 80 to be slidable therein, contoured stop members 90 can be provided on the proximal end 88 of the hollow needles 80. For example, the contoured stop members 90 could comprise an orienting surface 92 which slidably engages and generally follows the contour of the exterior surface of the second tube 30, as shown in FIG. 4. Such contoured stop members 90 would only allow the hollow needles 80 to be inserted into the lumens 54 in one rotational orientation. Preferably, the orienting surfaces 92 would be aligned with the beveled faces 84 of the hollow needles 80 such that the beveled faces 84 are always facing the central longitudinal axis 18. Furthermore, by properly axially positioning the stop members 90 on the hollow needles 80, the stop members 90 can act to limit the insertion depth of the hollow needles 80 into the lumens 54 to thereby insure that the distal tips 82 of the hollow needles 80 will be properly positioned within the cavities 44 at full insertion. It should be appreciated that, instead of stop members 90, other means for aligning the hollow needles 80 could be used, such as visual marks on the proximal end 88 of the hollow needles 80.

The suture material 100 in the disclosed embodiment includes a guide tip 102 attached to one end thereof to facilitate introduction of the suture material 100 through the hollow needles 80 and into the interior 28 of the first tube 20. The guide tip 102 acts as a lead for guiding the suture material through the hollow needles. Preferably, the guide tip 102 is a flexible cylindrical member that will deflect off of the wings 42 and into the opening 26 and, more preferably, the guide tip 102 comprises a flexible guidewire. Hollow cannulas 104 are utilized for pushing the guide tips 102 through the hollow needles 80. The exterior diameter of the hollow cannulas 104 is slightly smaller than the interior diameter of the hollow needles 80 such that the hollow cannulas 104 can freely slide inside the hollow needles 80. The interior diameter of the hollow cannulas 104 is large enough to allow the suture material 100 to freely pass therethrough, but is small enough to prevent the guide tips 102 from doing the same.

As an alternative to using hollow needles and cannulas, it should be appreciated that the means for inserting may comprise a non-hollow needle which is detachably connectable to the suture material 100 at the needle tip. In this regard, the needle may be inserted through the artery 12 wall and into the interior 28 of the first tube 20 while the suture material is secured to the needle tip. In this manner, the suture material would be inserted into the interior 28 of the first tube 20 at the same time the needle is being inserted. Accordingly, it would not be necessary to insert the suture material 100 through a hollow needle and may further not be necessary to use guide tips.

Figure 5:
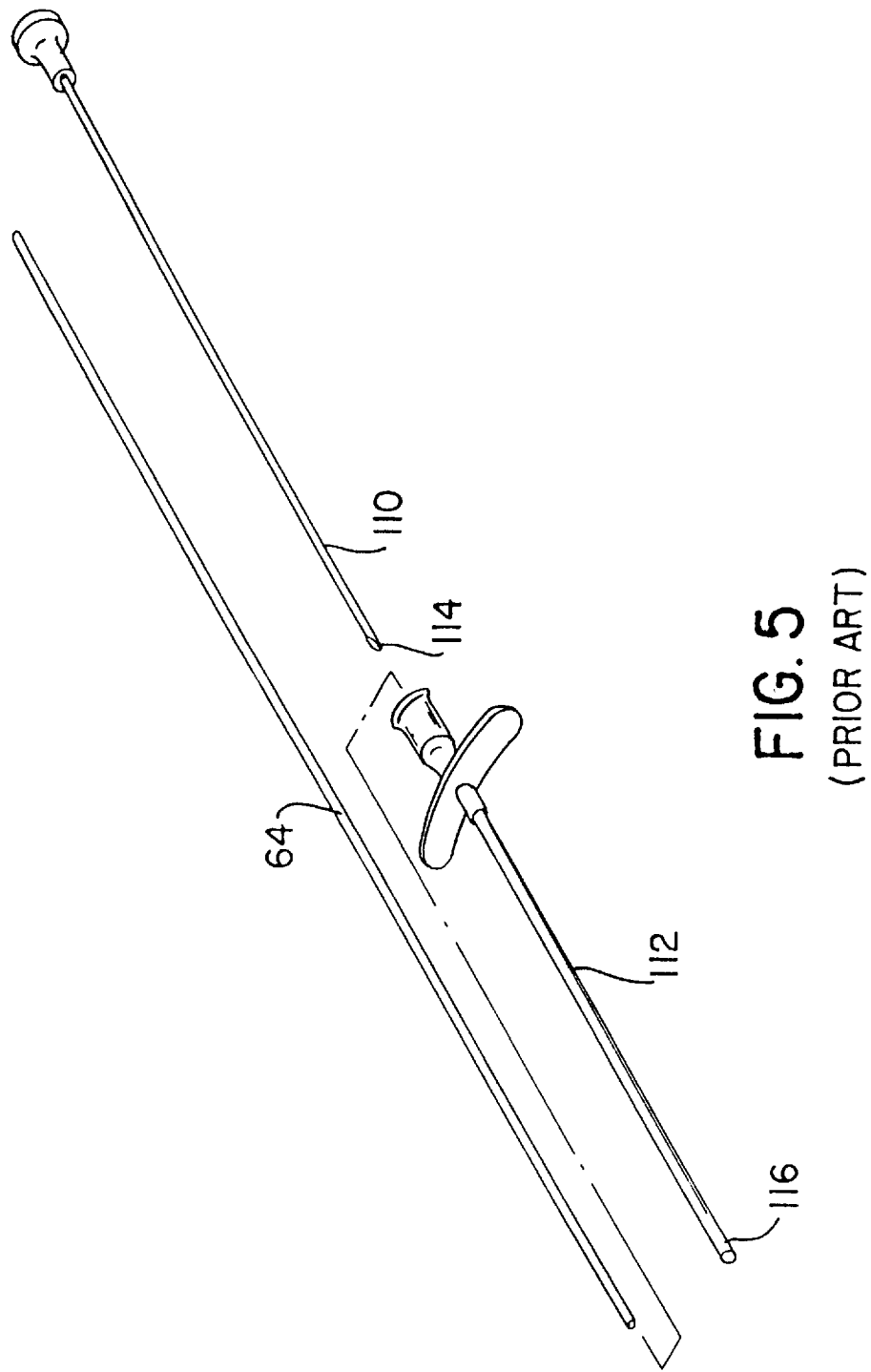
FIG. 5 is an exploded assembly view of an insertion needle and insertion cannula for introducing a guidewire into an artery.

Referring to FIGS. 2A–2F, the use and operation of the apparatus 10 embodying the present invention will now be described in connection with its use as an arterial catheter introducer inserted into an arterial wall 12 using a Seldinger technique. An insertion stylet 110 and insertion cannula 112 used in the Seldinger technique are shown in FIG. 5. In the Seldinger technique, the insertion stylet 110 is slidably positioned within the insertion cannula 112 such that the insertion stylet tip 114 aligns with the insertion cannula tip 116. The assembly is then inserted through the artery wall 12 until the insertion stylet tip 114 and cannula tip 116 are inside the artery 11. The insertion stylet 110 is then removed from the insertion cannula 112 and the guidewire 64 is inserted into the insertion cannula 112 until at least a portion of the guidewire 64 is similarly positioned inside the artery 11. The insertion cannula 112 is then removed, leaving only the guidewire 64 extending through the incision 14 into the interior of the artery 11.

With the dilator 70 fully inserted into the first tube 20 such that the distal end 74 of the dilator 70 extends beyond the first distal end 24, the apparatus 10 is threaded over the guidewire 64 (i.e., the dilator 70 is slid over the guidewire 64) and advanced toward the incision 14. Because of its conically-shaped distal end 74, when the dilator 70 reaches the incision 14, the dilator 70 will gradually stretch the incision 14 to facilitate insertion of the first and second tubes 20, 30 therein. The apparatus 10 is further inserted into the incision 14 until the artery wall 12 is positioned between the expandable portion 38 of the second tube 30 and the positioning member 50. That is, the apparatus 10 is positioned such that the openings 26 in the first tube 20 are inside the artery 11, as shown in FIG. 2A. The dilator 70 and guidewire 64 are subsequently removed to perform arterial catheter procedures.

After the catheter procedures have been performed, the dilator 70 and guidewire 64 are reintroduced into the first tube 20. It should be noted that, in order to have access to the proximal end 56 of the positioning member 50, the skin line 16 should be positioned distal to the proximal end 56 of the positioning member 50, as shown in FIG. 2A. In this regard, a positioning member 50 which is axially slidable on the second tube 30 is beneficial in that the positioning member 50 can be slid to accommodate different depths of the artery wall 12 relative to the skin line 16. Preferably, such a slidable positioning member 50 would not be rotatable relative to the second tube 30 so that the lumens 54 in the positioning member 50 remain aligned with the access holes 46 in the wings 42.

In order to perform the suturing procedure of the present invention, the apparatus should be positioned such that the lumens 54 are positioned on opposing sides of the incision. Next, the second proximal end 32 is moved distally relative to the first proximal end 22 to provide expansion of the expandable portion 38 from a retracted diameter to an expanded diameter larger than the retracted diameter, as shown in FIG. 2B. Such expansion results in wings 42 which define cavities 44 positioned over the openings 26 in the first tube 20. The hollow needles 80 are then partially inserted into the lumens 54 defined by the positioning member 50 and, using the contoured stop members 90 on the proximal end 88 thereof, the hollow needles 80 are oriented such that the beveled faces 84 of the distal tips 82 face toward the central longitudinal axis 18. The hollow needles 80 are further inserted into the lumens 54 to such a depth that the distal tips 82 pierce the artery wall 12 and enter the cavities 44 through the access holes 46, as shown in FIG. 2C. Proper insertion depth of the hollow needles 80 is insured by the stop members 90.

Figure 2D:
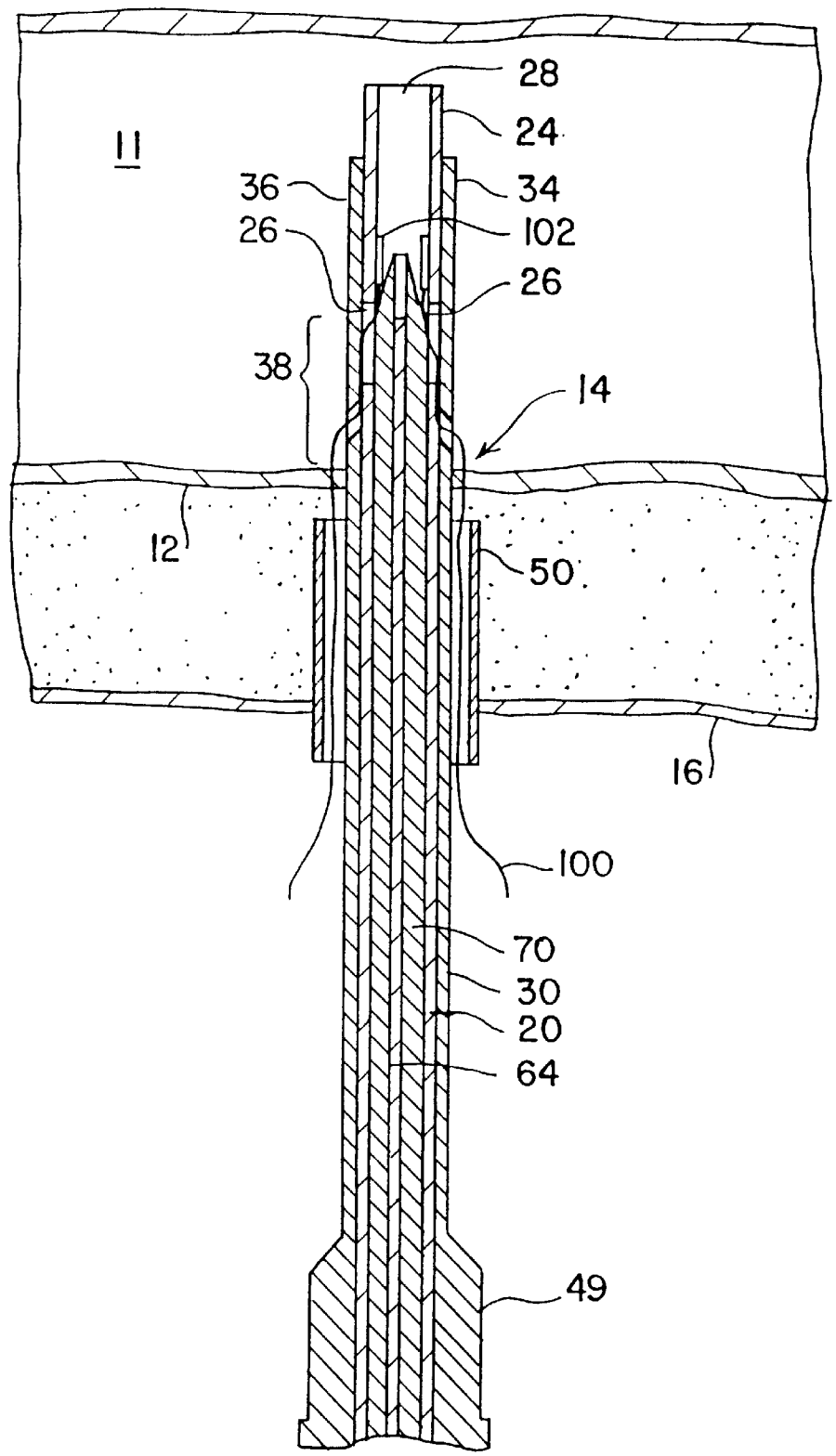
FIG. 2D is the section view of FIG. 2A with the apparatus in the retracted position and the suture material retained within the interior of the first tube.

The dilator 70 is subsequently retracted (i.e., moved proximally relative to the first tube 20) until the distal end 74 of the dilator 70 is positioned proximal to the openings 26 in the first tube 20. The guide tips 102 and attached suture material 100 are then inserted through the hollow needles 80 using the hollow cannula 104. Such insertion of the guide tips 102 continues until the guide tips 102 are inserted into the interior 28 of the first tube 20 through the openings 26, as shown in FIG. 2C. Next, the dilator 70 is advanced distally until the suture material 100 (e.g., the guide tips 102) is restricted between the distal end 74 of the dilator 70 and the interior 28 of the first tube 20, as shown in FIG. 2D. The hollow needles 80 and corresponding cannulas 104 are then retracted at least until the distal tips 82 of the hollow needles 80 and cannulas 104 are no longer inside the access holes 46. The expandable portion 38 is subsequently retracted by moving the second proximal end 32 proximally relative to the first proximal end 22. Misalignment of the access holes 46 relative to the openings 26 provides further restricting (i.e., in addition to the restricting provided by the dilator 70) of the suture material 100 and/or guide tips 102 to retain the suture material 100 in the interior 28 of the first tube 20, as further shown in FIG. 2D.

Figure 2E:
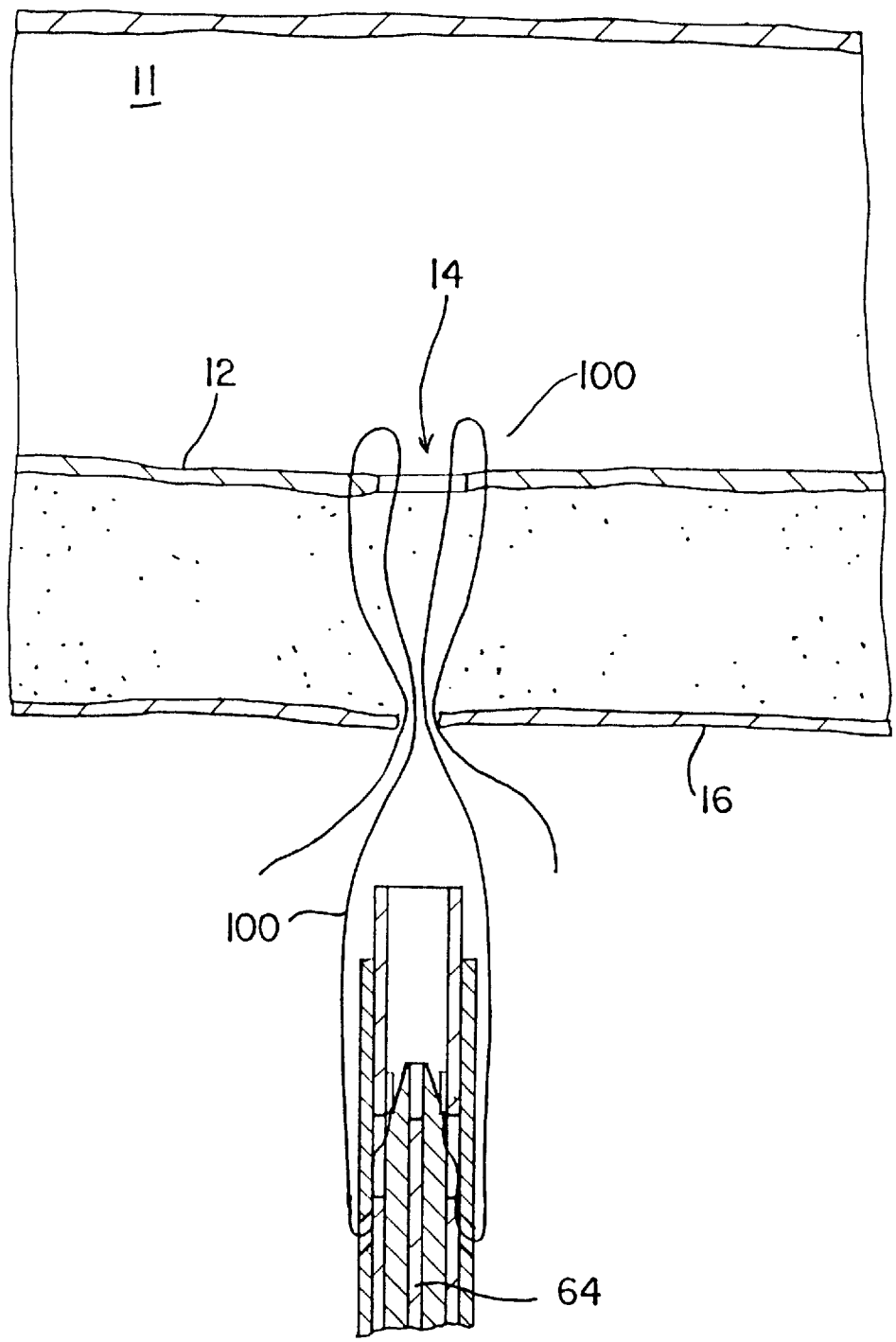
FIG. 2E is the section view of FIG. 2A showing the apparatus withdrawn from the incision to thereby pull the suture material back through the incision.

Subsequent removal of the apparatus 10 from the incision 14 results in the suture material 100 being withdrawn through the incision 14, as shown in FIG. 2E. The two ends of suture material 100 exiting the incision 14 (the inside ends 106) can be tied together and the two ends of the suture material 100 exiting the holes on either side of the incision 14 (the outside ends 108) can subsequently be tied to facilitate closure of the incision 14.

As an alternative to withdrawing the suture material 100 through the incision 14 by removing the apparatus 10 from the incision 14, the suture material 100 could be withdrawn by pulling it back through the interior 28 of the first tube 20. That is, the apparatus 10 could be provided with a means for engaging the suture material 100 and pulling the suture material out of the first tube 20 while the apparatus 10 stays inserted in the incision 14. For example, the means for engaging the suture material 100 may comprise an adhesive coated over the distal tip 74 of the dilator 70, such that the dilator 70 could be inserted into the first tube 20 to engage the suture material 100 and be withdrawn to withdraw the suture material back through the first tube 20 (and therefore back through the incision 14). Similarly, the dilator 70 (or any other member) could be supplied with a magnet or mechanical grip (e.g., a clamp, snare, or other device) for capturing the suture material 100 (including the guide tip 102) and withdrawing it back through the incision 14.

Figure 2F:
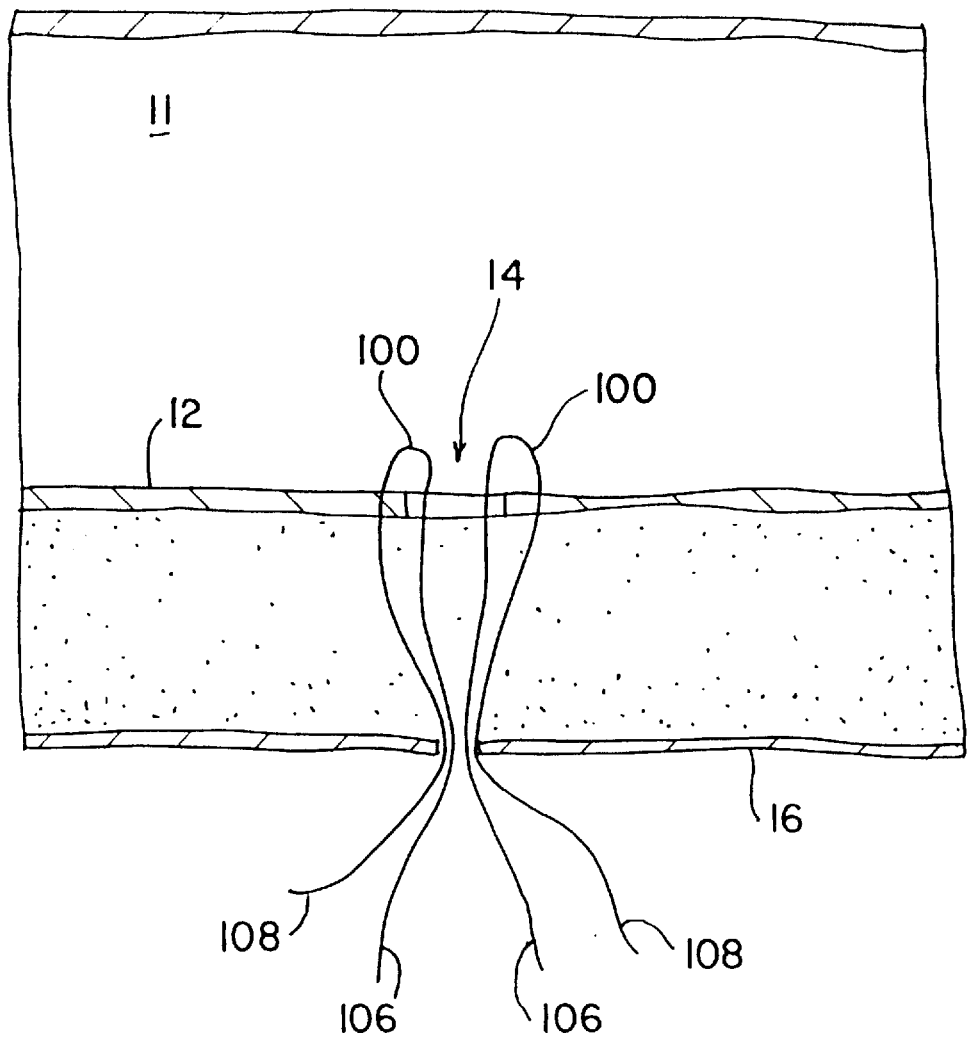
FIG. 2F is the section view of FIG. 2A showing the suture material threaded through the artery wall after the suture material is cut from the apparatus.

Because of the distal location of the incision 14 below the skin line 16, the incision 14 is typically not visible to the user of the apparatus 10, as generally represented in FIG. 2F. Accordingly, after removal of the apparatus 10 from the incision 14 and cutting of the suture material 100, as shown in FIG. 2F, it may be difficult for the user of the apparatus 10 to differentiate between the two inside ends 106 from the two outside ends 108 in order to facilitate closure of the incision. Furthermore, for other tieing techniques, it may be desirable to distinguish between the suture material 100 on one side of the incision 14 from the suture material 100 on the other side (i.e., right side versus left side). In order to alleviate the above-noted problems, suture material 100 may preferably be provided in which each of the four ends of suture material 100 is a different color. For example, referring to FIG. 2F, the suture material 100 entering through the artery wall 12 on one side of the incision 14 could be black with a white tip exiting the incision 14, and the suture material 100 entering through the artery wall 12 on the other side of the incision 14 could be blue with a green tip. Use of such suture material would facilitate distinguishing between each of the four ends of suture material 100 to assist in proper closure of the incision 14.

Figure 6:
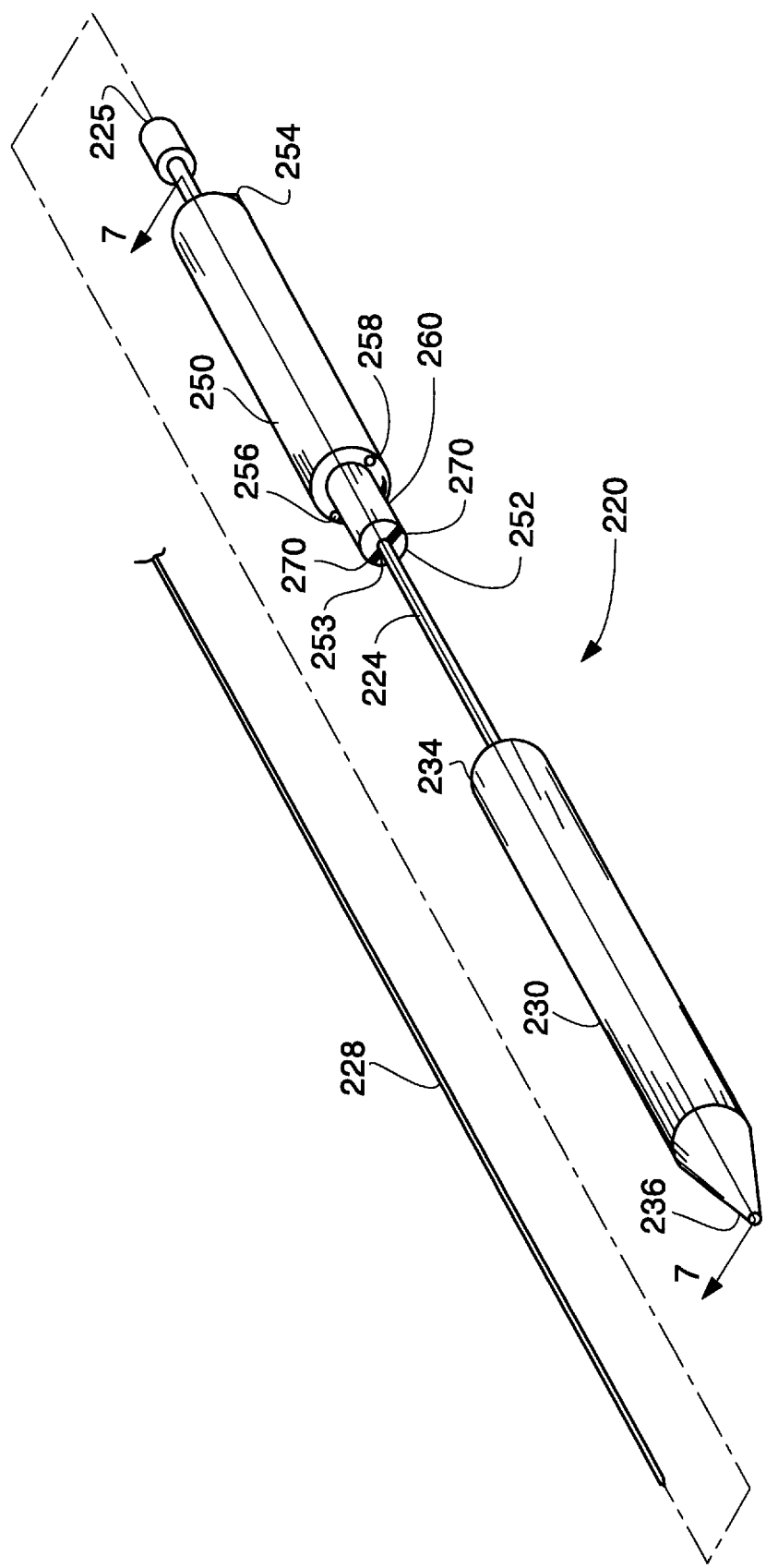
FIG. 6 is an exploded assembly view of an apparatus embodying another aspect of the present invention.

FIGS. 6–10 illustrate another embodiment of the present invention. Referring to FIG. 6, the apparatus 220 for use in suturing an incision in a tissue wall of a patient generally comprises a carrier member 224, a distal member 230 interconnected to the carrier member 224 and a guide member 250 positioned about and moveable along the carrier member 224. The guide member 250 functions as a guide for an access means comprising one or more single needles 280. In this regard, the guide member 250 is able to guide the single needle 280 through the tissue wall 290 at two or more different locations adjacent to the incision 292 such that suture material 300 is threadable through and into the tissue wall 290 at a first location 296 and back out of the tissue wall 290 at a second location 298.

More specifically, in one embodiment, the single needle 280 is selectively advanceable through the guide member 250 to make a first opening 295 in the tissue wall 290 at the first location 296, and, upon rotation of the rotatable guide member 250 about the carrier member 224, the single needle 280 is selectively advanceable to make a second opening 297 in the tissue wall at the second location 298 such that the suture material 300 is threadable through and into the tissue wall 290 at the first opening 295 and back out of the tissue wall 290 at the second opening 297.

Referring to FIGS. 6 and 7A–7E, the guide member 250 of the present embodiment is an elongated, hollow cylindrical member open at both a distal end 252 and a proximal end 254. The guide member 250 is slidably positionable over the carrier member 224 to facilitate axial and rotational movement of the guide member 250 about the carrier member 224. The inner diameter of the guide member 250 should be large enough to accommodate the carrier member 224 and the guidewire 228 within the carrier member 224, which will be described below. The inner diameter of the guide member 250 may range from about 0.016 inches to about 0.048 inches and the guide member 250 is preferably made from a polymer-based material such as polyolefin, polytetraflouroethylene, polyurethane and, most preferably, polyethylene.

To facilitate and properly guide access means into the tissue wall 290 at the first and second locations 296, 298, respectively, the guide member 250 preferably includes first and second lumens 256, 258, respectively, axially extending therethrough. As illustrated in FIGS. 7A–7E, the first and second lumens 256, 258 are symmetrically offset and equidistant from a centrally located longitudinal axis of the guide member 250 such that the first and second lumens 256, 258, respectively, are planar relative to each other and located approximately 180° from each other. As will be described below, the position and orientation of the first and second lumens 256, 258, respectively, within the guide member 250 preferably substantially correspond to the position and orientation of the first and second inlets 240, 242 of the proximal end 234 of the distal member 230. The first and second lumens 256, 258, respectively, are preferably cylindrical in cross-section, as shown in FIG. 6, and are preferably sized to receive a selectively advanceable and retractable single needle 280. In this regard, the diameter of the first and second lumens 256, 258 is preferably larger than the outer diameter of the single needle 280.

Referring to FIGS. 7A–7E, the distal end 252 of the guide member 250 includes a distal end portion 260. The distal end portion 260 releasably engages the guide member 250 with the proximal end 234 of the distal member 230, as will be described below. The distance between the distal end 252 on the distal end portion 260 and the main body 262 of the guide member 250 provides for an offset such that when the guide member 250 is releasably engaged with the distal member 230, the tissue wall 290 is not pinched or otherwise damaged. The distance between the distal end 252 of the distal end portion 260 and the main body 262 of the guide member 250 also provides for proper insertion depth of the single needle 280 into the first and second inlets 240, 242 of the distal member 230, as will be described below.

The distal member 230 is an elongated, hollow cylindrical member open at a distal end 236 and attached near a proximal end 234 to the carrier member 224. To facilitate proper positioning and insertion of the single needle 280 at the first and second locations 296, 298, respectively, the proximal end 234 of the distal member 230 includes an end portion for engaging the distal end 252 of the guide member 250, as will be described below. The distal end 236 of the distal member 230 is preferably conically shaped to facilitate insertion of the distal member 230 into the incision 292 in the artery tissue wall 290. For insertion of the distal member 230 into the interior of the artery, the distal member 230 is preferably slidably positionable over the guidewire 228. In this regard, the interior 238 of the distal member 230 should have a diameter large enough to accommodate the guidewire 228. For example, the interior 238 of the distal member 230 should have a diameter of ranging from about 0.016 inches to about 0.048 inches. Preferably, the distal member 230 is preferably made from a polymer-based material such as polyolefin, polytetraflouroethylene, polyurethane and, most preferably, polyethylene.

The distal end 252 of the guide member 250 is provided with a distal end portion 260 which interfaces with the proximal end 234 of the distal member 230. In order to provide for a substantially accurate insertion of the single needle 280 at first and second locations 296, 298, respectively, in the tissue wall 290, and to allow for rotation of the guide member 250 about a centrally located longitudinal axis of the carrier member 224, the interface or contact between the guide member 250 and the distal member 230 is preferably releasably engageable such that the guide member 250 may selectively guide the single needle 280 within the first lumen 256 into the tissue wall 290 at the first and second locations 296, 298, respectively, with minimal rotational or axial slippage of the guide member 250 about the carrier member 224 or relative to the distal member 230 as insertion occurs. Thus, once the first opening 295 in the tissue wall 290 is made by the advanceable single needle 280 within the first lumen 256 of the guide member 250, the engagement between the guide member 250 and the distal member 230 is preferably selectively releasable to allow rotation of the guide member 250 about the carrier member 224 and relative to the distal member 230 such that the advanceable single needle 280 in the first lumen 256 may make the second opening 297 in the tissue wall 290 at the second location 298.

In the illustrated embodiment, the proximal end 234 of the distal member 230 is cylindrical in cross-section and includes a female portion 244 and the distal end 252 of the guide member 250 is cylindrical and includes a male portion 264 such that the male portion 264 of the advanceable guide member 250 engages and/or is frictionally received within the female portion 244 of the distal member 230. In this regard, the outer diameter of the male portion 264 of the guide member 250 should be slightly less than the inner diameter of the female portion 244 of the distal member 230. Preferably, the engagement between the female and male portions 244, 264, respectively, is snug such that the portions 244, 264 do not disengage or otherwise slip during advancement of the single needle 280 into the tissue wall 290. Alternatively, as shown in FIG. 10, the distal end 252 of the guide member 250 may include a female portion 265 which frictionally engages a male portion 245 of the proximal end 234 of the distal member 230. In another embodiment, the respective male and female portions of the distal end 252 of the guide member 250 and proximal end 234 of the distal member 230 may be correspondingly tapered to provide for a frictional interface between the male and female portions.

The apparatus 220 may also include an aligning means to align the access means at two or more predetermined positions. The access means, comprising an advanceable single needle 280, which will be described below, is preferably alignable with a first and a second predetermined position corresponding to the first and second locations 296, 298 of the tissue wall 290. In this regard, the aligning means aligns the first lumen 256 of the guide member 250 at a first predetermined position corresponding to the first location 296 such that upon insertion of the advanceable single needle 280 through the tissue wall 290 at the first location 296, a portion of the distal end 282 of the single needle 280 is received within the first inlet 240 of the distal member 230. Upon rotation of the guide member 250 about the carrier member 224, the aligning means aligns the first lumen 256 and therefore the single needle 280 at a second predetermined position corresponding to the second location 298 such that upon insertion of the advanceable single needle 280 through the tissue wall 290 at the second location, the distal end 282 of the single needle 280 is received in the second inlet 242 of the distal member 230.

The aligning means may comprise a mechanical stop or, alternatively, a visual indicator of rotational position of the guide member 250, and more specifically, the angular rotational displacement of the first lumen 256 relative to the carrier member 224 and/or the distal member 230. In a preferred embodiment, the aligning means is a mechanical stop associated with proximal end 234 of the distal member 230 and the distal end 252 of the guide member 250. In this embodiment, to facilitate proper insertion of the single needle 280 into the tissue wall 290 at the desired locations, an aligning means is provided in the female portion 244 of the distal member 230 and on the male portion 264 of the guide member 250. The mechanical stop may comprise one or more protrusions (e.g., fins or tabs) and a corresponding slot or set of slots coplanar with the fins when aligned. One, or preferably two fins 270 may be associated with the face 253 of the distal ends 252 of the guide member 250 and one or more slots 246 coplanar with the fins 270 may be associated with the face 235 of the proximal end 234 of the distal member 230. The fins 270 of the guide member 250 and the slots 246 of the distal member 230 should be substantially planar relative to each other such that rotation of the guide member 250 will be stopped when the fins 270 are received in the slots 246. In this regard, the fins 270 of the guide member 250 and the slots 246 of the distal member 230 selectively stop rotation of the guide member 250 relative to the distal member 230 (and the carrier member 224) after approximately 180° rotation of the guide member 250 relative to the distal member 230.

Alternatively, where two sets of sutures are desired (e.g., to also include a set of sutures 90° offset from the first and second openings 295, 297), the proximal end 234 of the distal member 230 may include slots offset 90° from the slots 246. In this embodiment, a second recess (not shown) similar to the recess 247 may be provided in the distal member 230 to receive suture material 300 and to reverse its path. In addition, the guide member 250 may include third and fourth lumens to accommodate the second suture.

In an alternative embodiment, the aligning means may comprise first and second sets of fins associated with the proximal end 234 of the distal member 230 and the distal end 252 of the guide member 250, respectively. In this embodiment (not shown), the first set of fins may be positioned within the interior of the female portion 244 of the proximal end 234 of the distal member 230 and the second set of fins may be positioned on the face 253 or about the circumference of the distal end 252 of the guide member 250 such that when the guide member 250 is rotated from the first predetermined position 266 to a second predetermined position 268, the first and second sets of fins stop rotation of the guide member 250 relative to the carrier member 224 and therefore the distal member 230 after approximately 180° of rotation.

In an alternative embodiment of the present invention, the aligning means may be associated with the guide member 250 and the carrier member 224 since the carrier member 224 is connected to the distal member 230, as will be described below. The aligning means in this embodiment (not shown) may comprise stops, similar to the fins and corresponding slots disclosed above, wherein a first set of protrusions are associated with the carrier member 224 and at least one slot is associated with the guide member 250, or vice versa. Alternatively, the aligning means may comprise visual alignment indicators associated with the proximal end 254 of the guide member 250 and the carrier member 224 (not shown). In this embodiment, angular rotational indicators, such as markings on the guide member 250 and the carrier member 224 may comprise the aligning means to indicate when the guide member 250 has been rotated from a first predetermined position to a second predetermined position.

As illustrated in FIGS. 7A–7E, in order to accommodate receiving the distal end 282 of the single needle 280 upon advancement of the single needle 280, the proximal end 234 of the distal member 230 includes first and second inlets 240, 242. The first and second inlets 240, 242 are positioned about the proximal end 234 of the distal member 230 such that when the aligning means aligns the guide member 250 with the distal member 230 at the first and second predetermined positions, the inlets 240, 242 are aligned with the first lumen 256 of the guide member 250 at the first and second locations 296, 298, respectively. In this regard, the position of the first inlet 240 substantially corresponds with the first lumen 256 of the guide member 250 for insertion of the single needle 280 at the first location 296 such that when advanced to make the first opening 295 in the tissue wall 290, the distal end 282 of the single needle 280 is received in the first inlet 240. And, upon rotation of the guide member 250 to align the first lumen 256 at a second predetermined position, the position of the second inlet 242 substantially corresponds to the second location 298 such that the distal end 282 of the single needle 280 is received therein as the single needle 280 makes the second opening 297 in the tissue wall 290.

The single needle 280 of the present embodiment is an elongated, hollow cylindrical member open at both the distal end 282 and the proximal end 284. Because the single needle 280 will be used to facilitate insertion of the suture material 300 into the tissue wall 290, the single needle 280 is preferably large enough to accommodate the suture material 300 and guide tip 302 attached thereto, as will be described below. The distal end 282 of the single needle 280 preferably includes a beveled face 286. Preferably, for purposes of making the first and second openings 295, 297 in the tissue wall 290, the single needle 280 may be oriented such that the beveled face 286 faces away from a centrally located longitudinal axis of the guide member 250.

The suture material 300 in the present embodiment includes a guide tip 302 attached to one end thereof to facilitate introduction of the suture material 300 through the single needle 280 and through the tissue wall 290. In addition, the guide tip 302 acts as a lead for guiding the suture material 300 about the distal member 230, and back out through the tissue wall 290, as will be described below. Due to the flexible nature of the guide tip 302, the guide tip 302 guides the suture material 300 about a recess 247 in the distal member 230 such that the path of the suture material 300 is reversable within the distal member 230, as will be described below. The guide tip 302 includes first and second ends 306, 308, respectively, with the second end 308 being attached to the suture material 300. Since the guide tip 302 is incrementally advanceable within the guide member 250 and the distal member 230, it is preferably of a length sufficient to extend from the proximal end of the first lumen 256, through the recess 247 of the distal member 230, and back out through the second lumen 258 of the guide member, such that the first and second ends 306, 308 of the guide tip 302 extend proximally from proximal end 254 of the guide member 250. In this embodiment of the invention, the length of the guide tip 302 ranges from about 1 inch to about 18 inches. In a preferred embodiment, the guide tip 302 comprises a flexible guidewire. Preferably, the guide tip 302 is a flexible cylindrical member having a diameter ranging from about 0.006 inches to about 0.038 inches.

Figure 8:
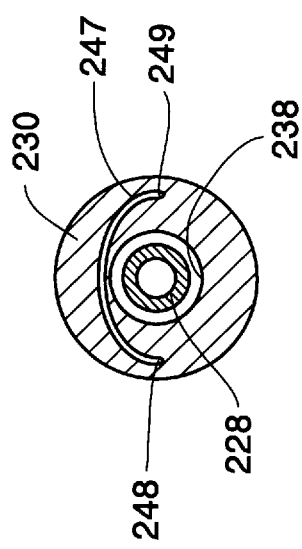
FIG. 8 is a section view taken along line 8—8 in FIG. 7A.

In order to facilitate threading of the suture material 300 within the tissue wall 290 (i.e., between the first and second openings 295, 297, respectively), the distal member 230 includes a recess 247 therein. The recess 247 provides a means within the artery for reversing the path of the suture material 300 such that the suture material 300 may enter the tissue wall 290 through the second opening 295 and exit the tissue wall 290 through the first opening 297. In one embodiment, as illustrated in FIG. 8, the recess 247 is substantially arcuate and extends over the interior 238 of the distal member 230. In this regard, after the suture material 300 and guide tip 302 thereon are received from the single needle 280 through the second opening 297 of the tissue wall 290, the recess 247 provides a path by which the guide tip 302 leads the suture material 300 from the first end 248 of the recess 247, over the interior 238 of the distal member 230 (which carries the guide wire 228 therein), and out of the second end 249 of the recess 247. Alternatively, the recess 247 may provide an arcuate path about the distal member 230 wherein the recess 247 provides a path from the first end 248 to the second end 249 beneath the interior 238 of the distal member 230.

Figure 7A:
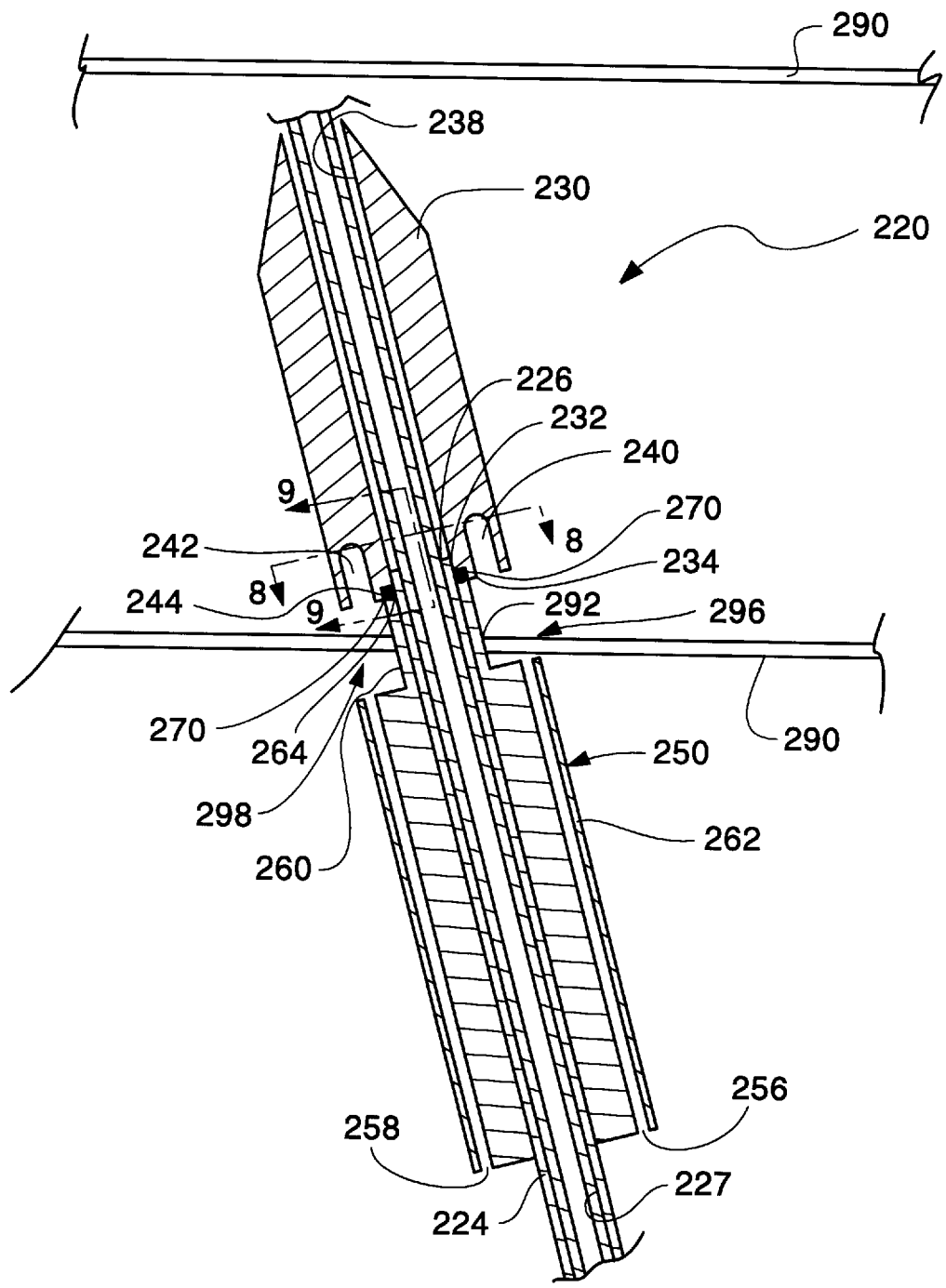
FIG. 7A is a longitudinal section taken along line 7—7 in FIG. 6 with the apparatus inserted into an incision in an artery wall.
Figure 7B:
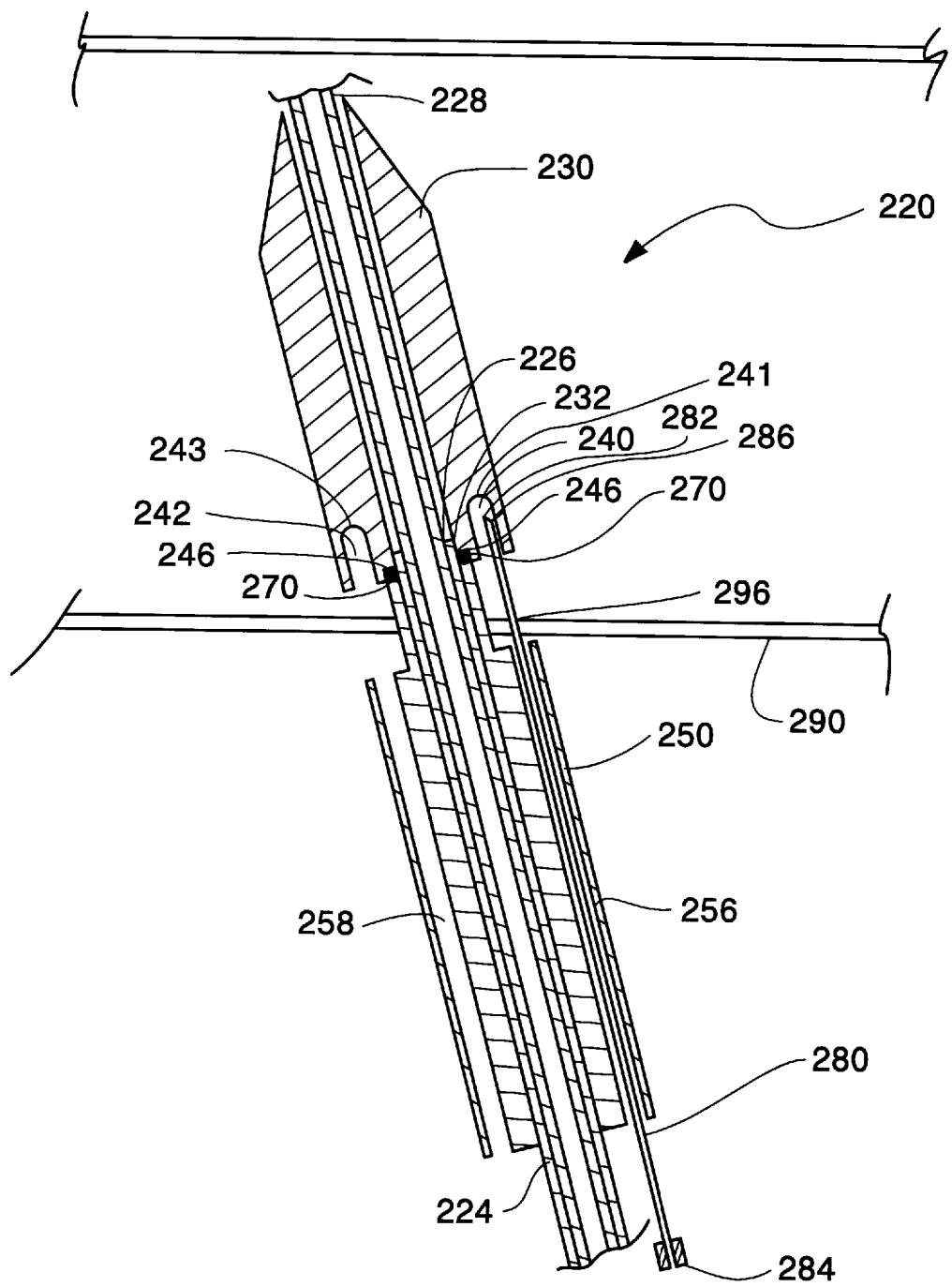
FIG. 7B is the section view of FIG. 7A showing the guide member guiding a single needle through the tissue wall adjacent the incision at a first location.
Figure 7C:
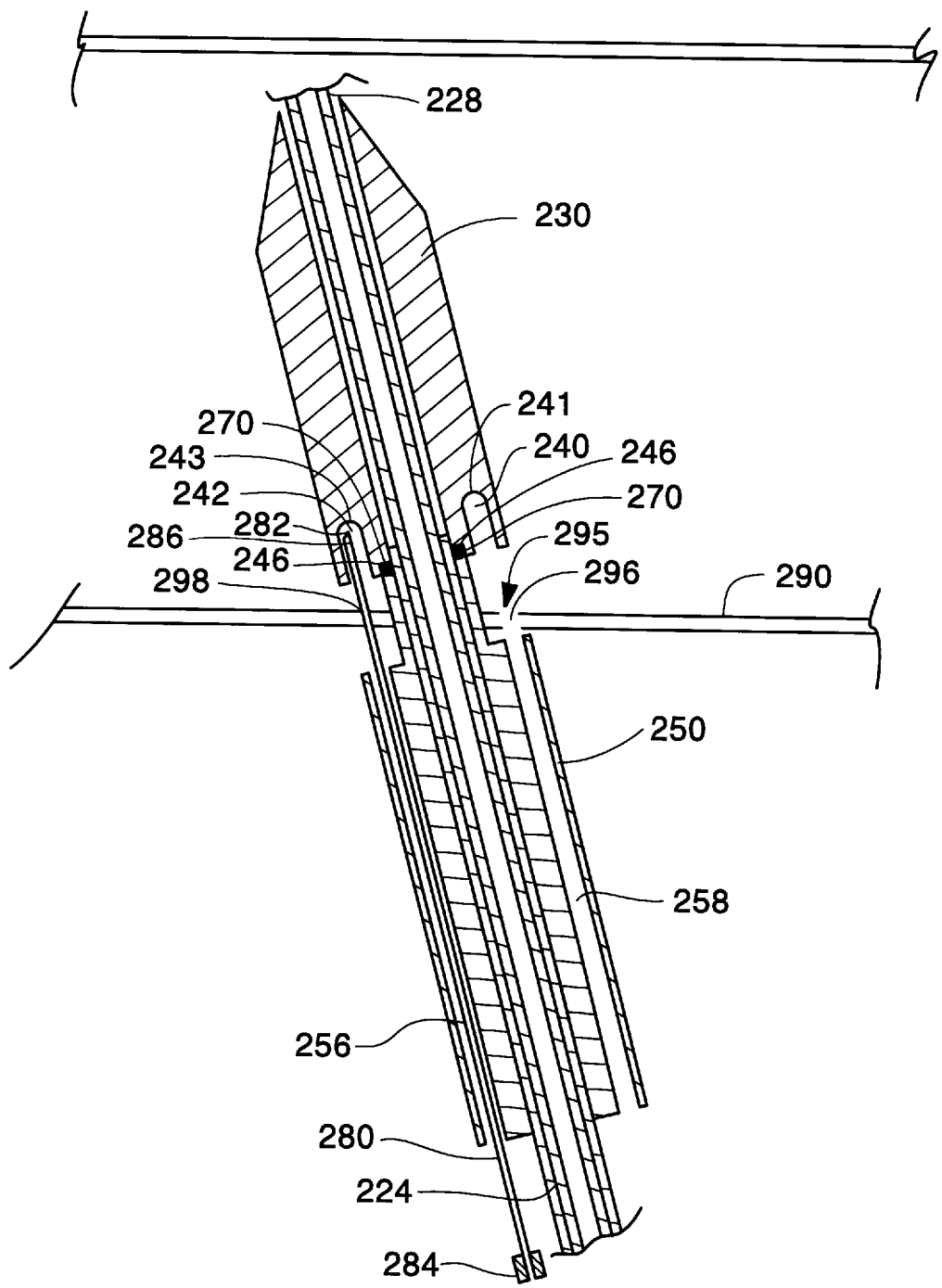
FIG. 7C is the section view of FIG. 7A showing the rotated guide member guiding the single needle through the tissue wall adjacent the incision at a second location.
Figure 7D:
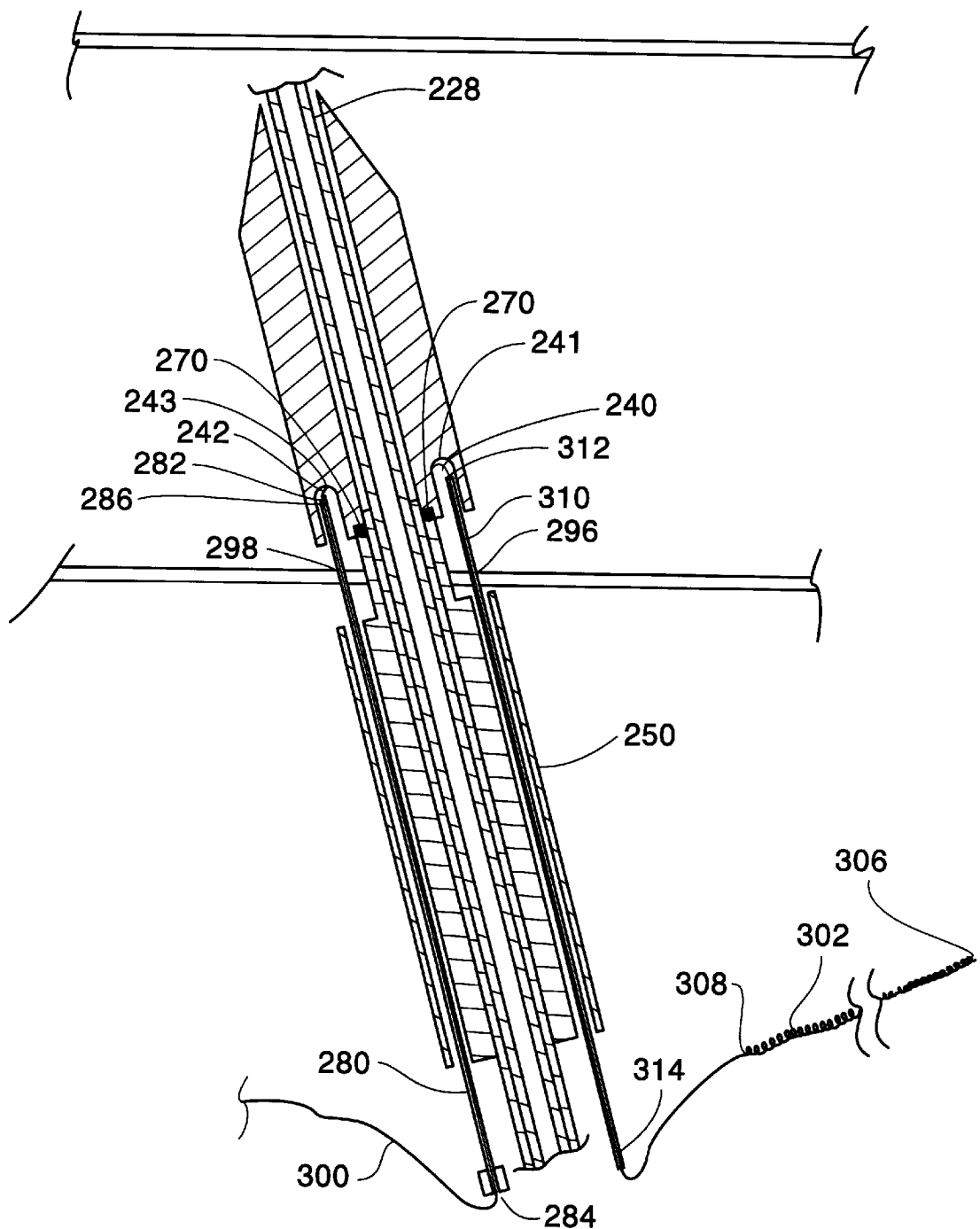
FIG. 7D is the section view of FIG. 7A showing the threading of the suture material into the first opening of the tissue wall through a tube within the second lumen of the guide member and back out of the second opening of the tissue wall through the single needle.
Figure 7E:
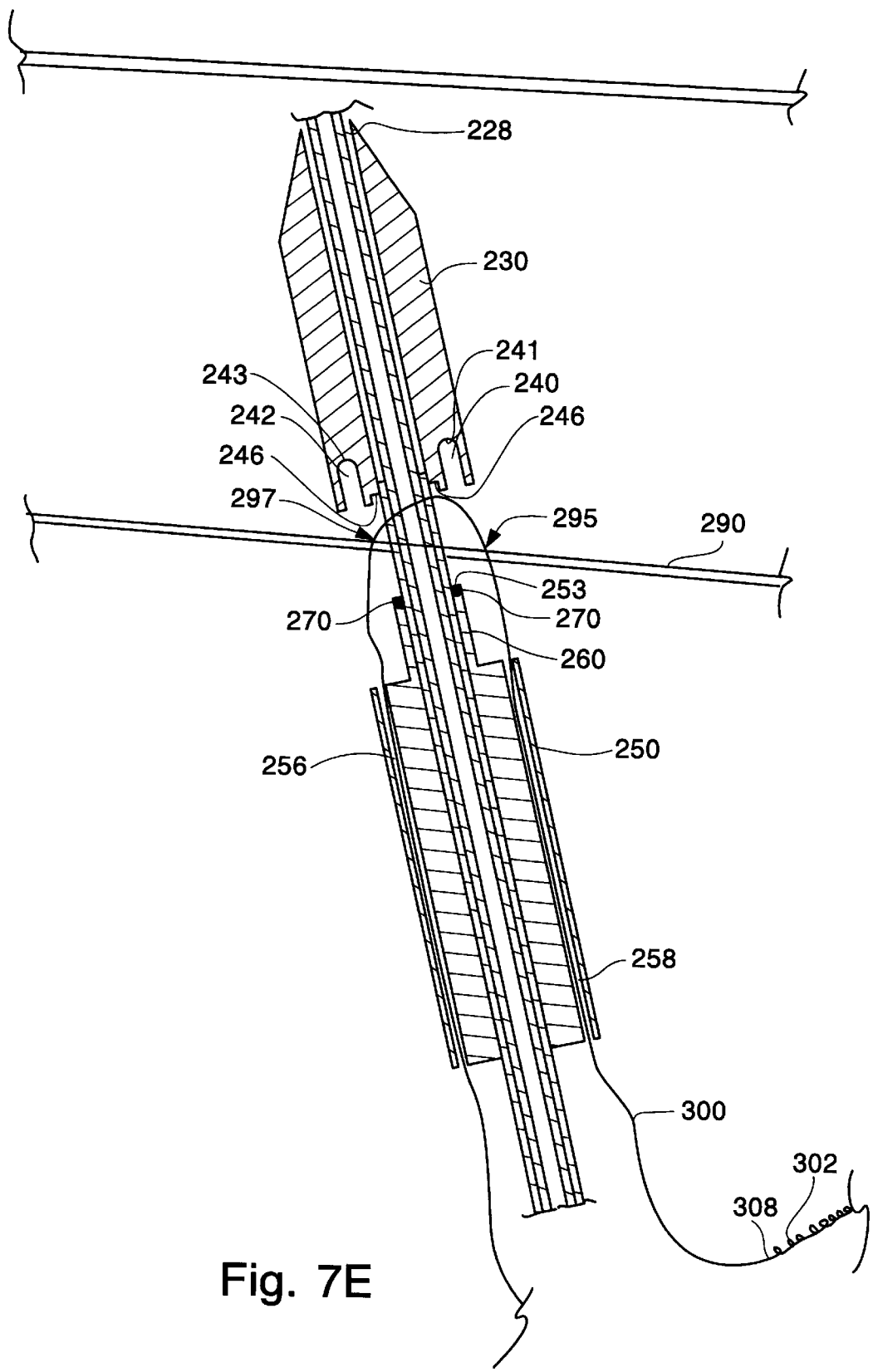
FIG. 7E is the section view of FIG. 7A showing the guide member withdrawn from the incision and the suture material threaded through the artery.
Figure 9:
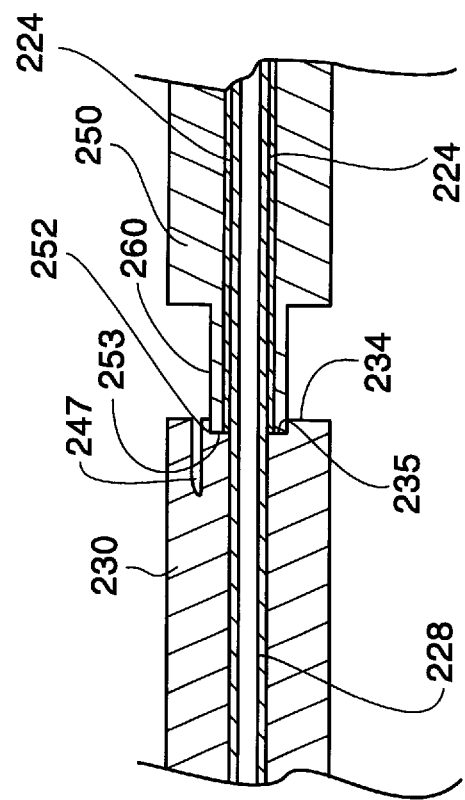
FIG. 9 is a section view taken along line 9—9 in FIG. 7A.

In order to reverse the path of the suture material 300 and the guide tip 302 thereon within the distal member 230, the recess 247 may comprise an open, arcuately shaped groove which generally extends distally from the proximal end 234 of the distal member 230 toward the distal end 236 of the distal member 230. In this regard, the recess 247 extends arcuately over (or, alternatively, beneath) the interior 238 of the distal member 230, between the first and second inlets 240, 242 of the distal member 230, and extends distally from the proximal end 234 of the distal member 230, substantially as shown in FIGS. 8 and 9. Thus the recess 247 comprises an arcuate groove within the distal member 230 extending between the first and second inlets 240, 242, wherein the recess 247 is open to the proximal end 234 of the distal member 230 between the first and second inlets 240, 242. As will be discussed below, the recess 247 thus provides for a selective release of the suture material 300 from the distal member 230, as shown in FIG. 7E. Preferably, the recess 247 is sized to accommodate receiving a portion of the guide tip 302 of the suture material 300 so as to guide the suture material 300 and the guide tip 302 thereon about the distal member 230 from the first end 248 to the second end 249 of the recess 247.

For purposes of facilitating insertion and extrusion of the distal member 230 into and out of the artery, the distal member 230 is associated with the carrier member 224, which will be described below. More specifically, the distal member 230 and the carrier member 224 are connected to each other and are slidably positionable over the guidewire 228 contained therein. The proximal end 234 of the distal member 230 is associated with the distal end 226 of the carrier member 224. In this regard, a portion of the distal end 226 of the carrier member 224 is interconnected with a first part 232 of the proximal end 234 of the distal member 230. The distal end 226 of the carrier member 224 and the first part 232 of the proximal end 234 of the distal member 230 may be molded together or, alternatively, the interconnection may be of a mechanical or chemical nature. In particular, the distal end 226 of the carrier member 224 may be connected to the proximal end 234 of the distal member 230 by fasteners, melding, fusing, adhesives, such as non-toxic glues, and thermal or solvent bonding techniques. The proximal end 225 of the carrier member 224 is preferably enlarged so that the carrier member 224 can be gripped by the user and selectively moved about the guidewire 228 along with the distal member 230.

The carrier member 224 of the present invention is an elongated, hollow cylindrical member open at both a proximal end 225 and a distal end 226 and having a central longitudinal axis. The interior 227 of the carrier member 224 should have a diameter large enough for insertion of a guide wire 228 appropriately sized for the specific application. For example, the interior 227 of the carrier member 224 should have an inner diameter ranging from about 0.016 inches to about 0.042 inches to accommodate a guide wire 228 having an outer diameter in the range of about 0.014 inches to about 0.038 inches. The carrier member 224 is preferably made from a polymer-based material such as polyolefin, polytetraflouroethylene, polyurethane and, most preferably, polyethylene.

In order to perform the suturing procedure of the present invention, the distal member 230 of the apparatus 220 is moved distally via the carrier member 224 along the guide wire 228 therethrough, through the incision 292 in the artery tissue wall 290 and into the artery. Next, the guide member 250 is moved distally relative to the carrier member 224 to contact the proximal end 234 of the distal member 230 such that the proximal end 234 of the distal member 230 releasably engages the distal end 252 of the guide member 250, as described above. Preferably, in order to ensure that the first and second openings 295, 297, respectively, are positioned on opposite sides of the incision 292, substantially 180° from each other, the fins 270 of the distal end 252 of the guide member 250 should initially engage the slots 246 of the proximal end 234 of the distal member 230 such that the first and second lumens 256, 258 are substantially aligned with the first and second locations 296, 298, respectively of the tissue wall 290 and with the first and second inlets 240, 242 of the distal member 230. In addition, to provide for a stable interface between the guide member 250 and the distal member 230 during advancement of the single needle 280, the male portion 264 at the distal end 252 of the guide member 250 should snugly engage (i.e., frictionally) the female portion 244 at the proximal end 234 of the distal member 230. The access means comprising a single needle 280 may then be inserted into the first lumen 256 of the guide member 250 and then advanced through the tissue wall 290 at the first location 296 to make the first opening 295, as shown in FIG. 7B. The single needle 280 may be advanced until it is substantially received within the first inlet 240 of the distal member 230, or, alternatively, until the distal end 282 of the single needle 280 contacts the distal end 241 of the inlet 240.

Once the first opening 295 has been made, the single needle 280 may be retracted from the tissue wall 290. In this embodiment, the single needle 280 remains within the first lumen 256. In order to make the second opening 297 in the tissue wall 290, the guide member 250 is rotated 180° relative to the distal member 230. This is accomplished by disengaging the proximal end 234 of the distal member 230 from the distal end 252 of the guide member 250. In this regard, for purposes of minimizing trauma to the tissue wall 290 and associated blood loss, to efficiently disengage the guide member 250 from the distal member 230, the carrier member 224 (which is connected to the distal member 230)

may be gripped, preferably at its proximal end 225, while the guide member 250 is moved proximally. Once the fins 270 of the guide member 250 have been disengaged from the slots 246 of the distal member 230, the guide member 250 may be rotated about and relative to the carrier member 224 and the distal member 230 until the first lumen 256 (which contains the single needle 280) is aligned with the second location 298 and the second inlet 242. Alignment substantially occurs as the guide member 250 is rotated relative to the distal member 230 when the fins 270 of the guide member 250 substantially engage the slots 246 of the distal member 230. Once engaged, the guide member 250 may be moved distally relative to the carrier member 224 and distal member 230 to ensure a snug fit between the female portion 244 at the proximal end 234 of the distal member and the male portion 264 at the distal end 252 of the guide member 250. The single needle 280 may then be moved distally through the tissue wall 290 at the second location 298 to make the second opening 297, as shown in FIG. 7C. The single needle 280 may be advanced until the distal end 282 of the single needle 280 is received in the second inlet 242 or, alternatively, until the distal end 282 contacts the distal end 243 of the second inlet 242.

Suture material 300 may then be threaded through and into the second opening 297 of the tissue wall 290 by distally advancing the first end 306 of the guide tip 302 through the interior of the single needle 280 (which is contained within the first lumen 256). The first end 306 of the guide tip 302 may be advanced by feeding consecutive proximal portions of the guide tip 302 into the single needle 280. Upon advancement through the second opening 297, the first end 306 of the guide tip 302 then enters the second inlet 242 and the first end 248 of the recess 247. Upon entry into the recess 247, the first end 306 of the guide tip 302 is guided within the recess 247 about the distal member 230, and in particular, over the interior 238 of the distal member 230, such that the path of the guide tip 302 is reversed. In this regard, as the guide tip 302 continues to advance, the guide tip 302 starts moving proximally, toward the second end 249 of the recess 247 such that it is received within the first inlet 240 of the distal member 230.

In order to facilitate exit of the suture material 300 from the tissue wall at the first opening 295 and through the second lumen 258 of the guide member 250, an elongated, hollow cylindrical tube 310 having distal and proximal ends 312, 314, respectively, may be inserted into the second lumen 258 of the guide member 250 such that a distal end 312 of the tube 310 advances through the first opening 295 and is received within the first inlet 240. In this regard, tube 310 is long enough to extend beyond the proximal end 254 of the guide member 250 when inserted through the first opening 295 and into the first inlet 240. The tube 310 is preferably large enough to receive the guide tip 302 subsequent to the guide tip 302 entering the first inlet 240. Thus, consecutive proximal portions of the guide tip 302 may be fed through the first lumen 256 of the guide member 250 until the first end 306 of the guide tip 302 exits the proximal end 314 of the tube 310 (which is contained within the second lumen 258). Once the first end 306 exits the proximal end 314 of the tube 310, the first end 306 may be grasped and pulled proximally such that suture material 300 is fed through second and then first openings 297, 295, respectively, as shown in FIG. 7D.

Next, the guide member 250 may be disengaged from the distal member 230 and withdrawn from the incision 292 by moving the guide member 250 proximally relative to the carrier member 224 and distal member 230. Because the recess 247 of the distal member 230 is open at the proximal end 234 of the distal member 230, the suture material 300 may then be "slipped" or pulled out of the recess 247, as shown in FIG. 7E. At this point, the above-described procedure may be repeated with the apparatus 220, if desired, in order to suture the incision at openings 90° offset from the first and second openings 295, 297. In this regard, the apparatus 220 would be rotated 90° and the procedure repeated.

The distal member 230 and carrier member 224 may then be moved proximally, out of the artery, through the incision 292. Once the apparatus 220 has been removed from the interior of the artery, portions or ends of the suture material 300 can be grapsed proximal the tissue wall and withdrawn proximally or pulled in order to test the position and stability of the suture material about the incision and within the first and second openings 295, 297 in the tissue wall. Portions or ends of the suture material 300 may then be tightened and tied together to facilitate closing of the incision 292 and to complete the suture.

Figure 11:
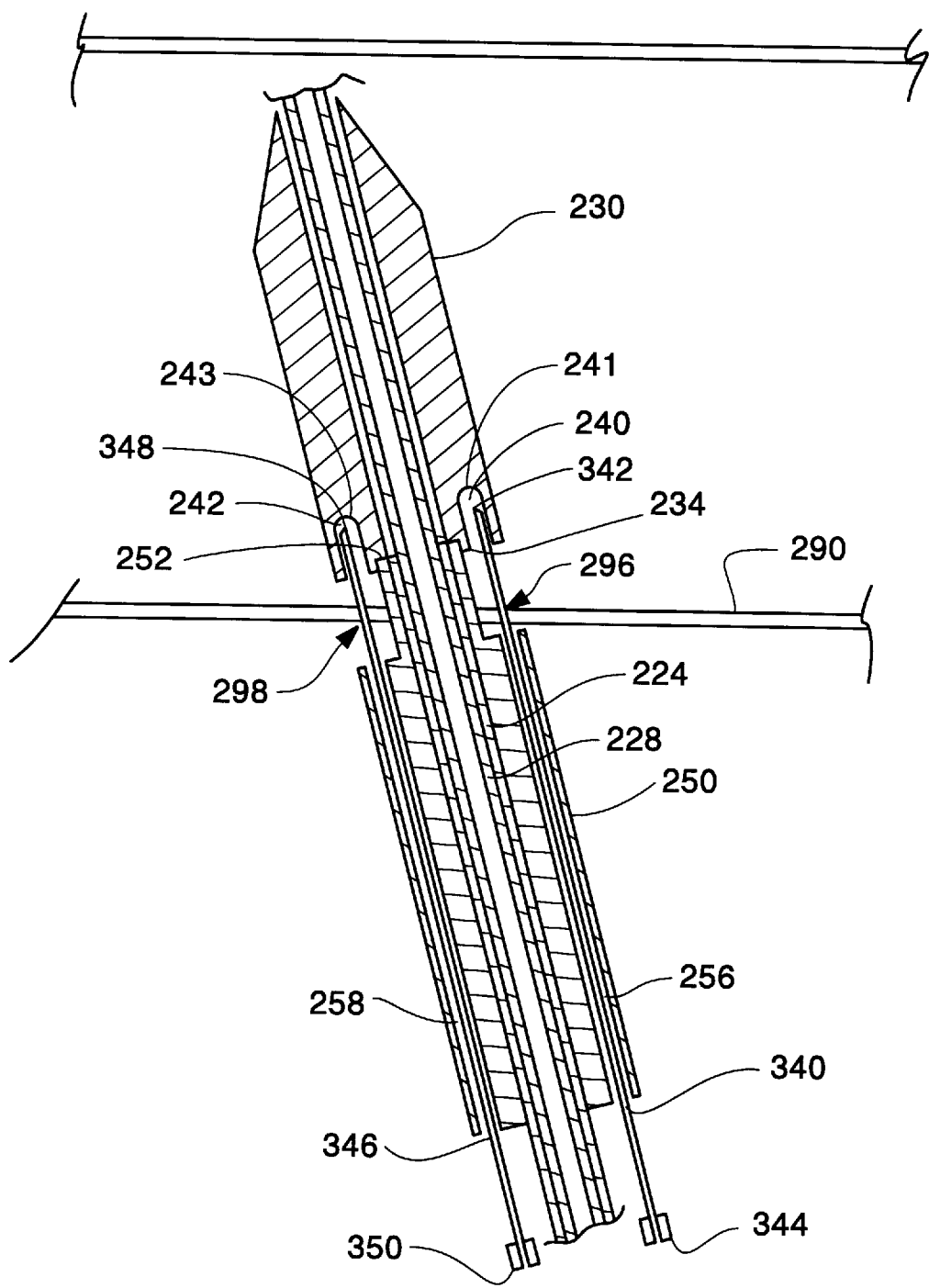
FIG. 11 is a section view of another embodiment of the present apparatus.

In another embodiment, illustrated in FIG. 11, the apparatus 220 may be used with first and second hollow, cylindrical needles 340, 346 having distal and proximal ends 342, 348 and 344, 350, respectively. Once the first and second lumens 256, 258 are substantially aligned with the first and second locations 296, 298 and the first and second inlets 240, 242 of the distal member 230, the first and second needles 340, 346 may be inserted simultaneously, or consecutively, into first and second lumens 256, 258 of the guide member 250 and advanced such that first and second needles 340, 346 are inserted through the tissue wall 290 at first and second locations 296, 298 to make first and second openings 295, 297. In this regard, the first and second needles 340, 346 may be advanced until the distal ends 342, 348 are substantially received within the first and second inlets 240, 242, respectively, or, until the distal ends 342, 348 contact the distal ends 241, 243 of the first and second inlets 240, 242.

Next, the first end 306 of the guide tip 302 may be inserted into one of the first and second needles 340, 346 for purposes of suturing the incision. For example, the first end 306 of the guide tip 302 may be inserted into the proximal end 344 of the first needle 340 and advanced distally towards the first opening 295 in the tissue wall 290. Consecutive proximal portions of the guide tip 302 may be fed into the first needle 340 in order to move the first end 306 of the guide tip 302 through the tissue wall 290 and into the first inlet 240. As the first end 306 continues to advance distally, it is received within the second end 249 of the recess 247 and guided about the distal member 230, substantially as described above. In this regard, the recess 247 reverses the direction of the first end 306 of the guide tip 302 such that the first end 306 advances proximally. Upon exit from the first end 248 of the recess 247, the first end 306 of the guide tip 302 is received within the distal end 348 of the second needle 346 within the second lumen 258. As consecutive proximal portions of the guide tip 302 continue to be fed into the first needle 340 within the first lumen 256, the first end 306 of the guide tip 302 advances proximally toward the proximal end 350 of the second needle 346. Upon exit of the first end 306 of the guide tip 302, suture material 300 connected to the second end 308 of the guide tip 302, may be threaded through the first and second openings 295, 297 in the tissue wall 290. Substantially as described above, the guide member 250 may then be disengaged from the distal member 230 in order to "slip" the suture material 300 from the recess 247 of the distal member 230. The carrier member 224 and the distal member 230 may then be removed from the incision 292, as may the guide wire 228. Then the ends or portions of the suture material 300 may be grasped and withdrawn proximally or pulled in order to test the position and stability of the suture about the incision. The ends or portions of the suture material 300 may then be tightened and tied to suture the incision 292.

Figure 12:
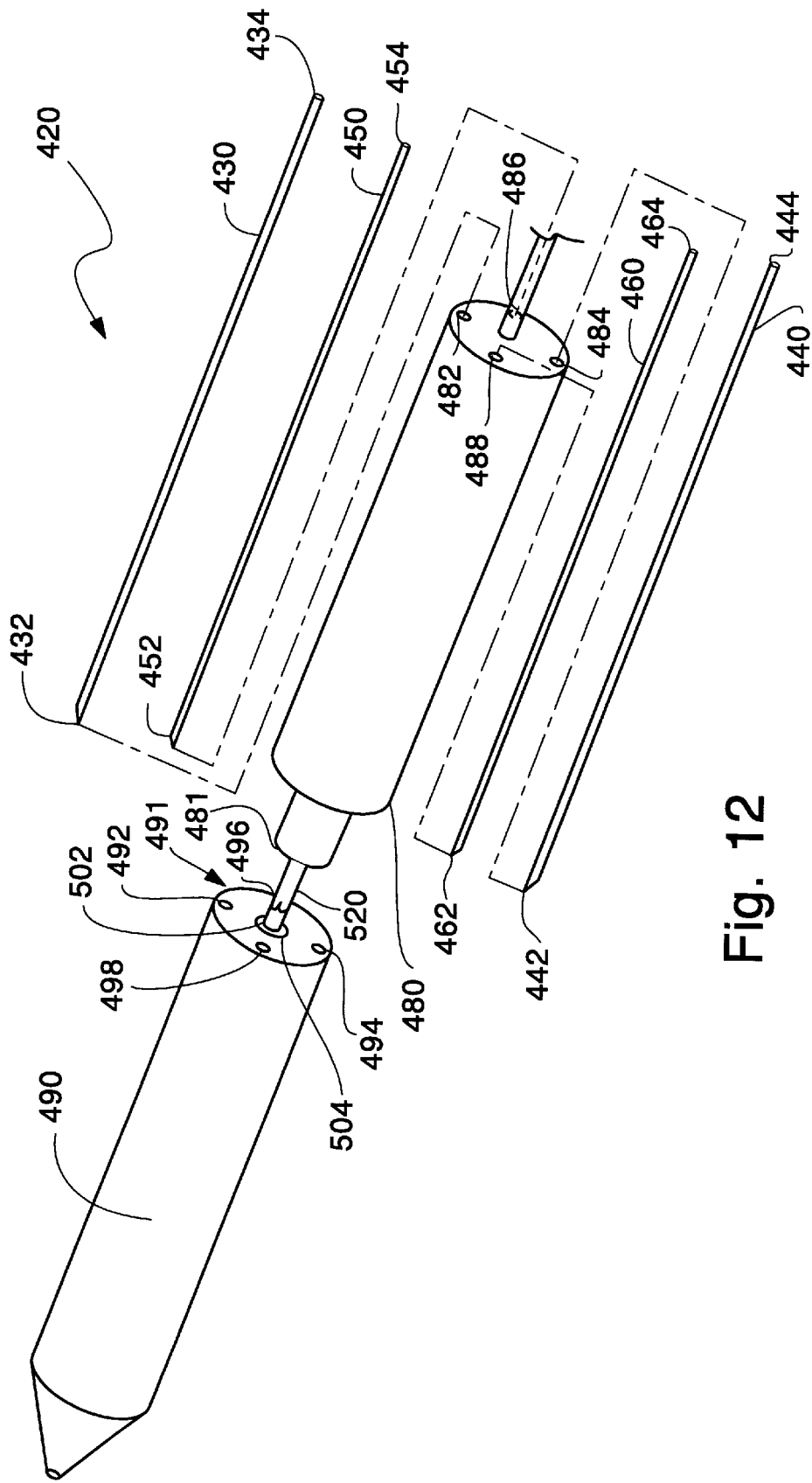
FIG. 12 is a perspective view of another embodiment of the present apparatus.

In an alternative embodiment, illustrated in FIG. 12, the apparatus 420 may be used to close the incision with two sutures disposed approximately 90° from each other. In this embodiment, the apparatus 420 may include first, second, third, and fourth hollow, cylindrical needles 430, 440, 450, 460, each having distal and proximal ends 432, 434, 442, 444, 452, 454, 462, 464, respectively. These needles may be received within first, second, third and fourth lumens 482, 484, 486, 488 of the guide member 480, respectively. In order to pierce the tissue wall of the artery at four separate predetermined locations (not shown) located substantially 90° from each other, the guide member 480 may align the first, second, third and fourth lumens 482, 484, 486, 488 with the four locations and with the first, second, third and fourth inlet areas 492, 494, 496, 498, respectively, at the proximal end 491 of the distal member 490.

As described above, this alignment may be substantially accomplished by engaging the distal end 481 of the guide member 480 with the proximal end 491 of the distal member 490. More specifically, the fins or tabs (not shown) on the distal end 481 of the guide member 480 may be engaged within the slots 502, 504 at the proximal end 491 of the distal member 490. Once first, second, third and fourth lumens 482, 484, 486, 488 are aligned with the first, second, third, and fourth inlet areas 492, 494, 496, 498 of the distal member 490, respectively, the first, second, third and fourth needles 430, 440, 450, 460 may be inserted simultaneously or consecutively into the first, second, third and fourth lumens 482, 484, 486, 488 of the guide member 480, respectively, and advanced such that the needles are inserted through the tissue wall at the four predetermined locations to make four openings in the tissue wall (not shown). In this regard, the needles 430, 440, 450, 460 may be advanced until the distal ends 432, 442, 452, 462 of the needles are substantially received within the inlets 492, 494, 496, 498, respectively, of the distal member 490.

Next, the first end(s) of one or more guide tips (not shown) may be inserted simultaneously or consecutively into the proximal end of one of the first and second needles 430, 440 and into the proximal one of the third and fourth needles 450, 460 for purposes of threading two sutures about the incision. For example, substantially as described above, the first ends of the guide tips may be inserted into the proximal ends 434, 454 of the first and third needles 430, 450 and advanced distally towards the respective openings in the tissue wall. Consecutive proximal portions of the guide tip may be fed into the first and third needles 430, 450 in order to move the first ends of the guide tips through the tissue wall and into the first and third inlets 492, 496 of the distal member 490. As the first ends continue to advance distally, they are received within the recesses (not shown) of the distal member and guided about the distal member 490 substantially as described above, except that such recesses are disposed generally 90° from each other. In this regard, the recesses reverse the direction of the guide tips such that the first ends of the guide tips advance proximally.

Upon exit from the recesses, the guide tips exit the inlets 494, 498 and are received within tubes or needles 440, 460, respectively, within the second and fourth lumens 484, 488 of the guide member 480. As consecutive proximal portions of the guide tips continue to be fed into the first and third needles 430, 450, the first ends of the guide tips advance towards the proximal ends 444, 464 of the second and fourth needles 440, 460. Upon exit of the first ends of the guide tips from the proximal ends 444, 464 of the second and fourth needles 440, 460, suture material connected to a second end of the guide tip (not shown) may be threaded through the four openings in the tissue wall by proximally advancing or pulling the first ends of the guide tips. Substantially, as described above, the guide member 480 may be disengaged from the distal member 490 in order to "slip" the suture material from the recesses of the distal member 490. The carrier member 520 and the distal member 490 may then be removed from the incision, as may the guide wire. Then the ends of the suture material may be grasped to move the suture material towards the incision in order to test the position and stability of the suture material about the incision. The suture material may then be tightened and tied to close the incision with two sutures.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. An assembly for use in suturing an incision in a tissue wall of a patient with a suture material, said assembly comprising:

a carrier member;

a distal member interconnected to said carrier member, said distal member and interconnected carrier member being positionable at least partially through the incision inside the tissue wall; and a guide member rotatable about and movable along said carrier member and having at least a first lumen extending therethrough for guiding a needle through said first lumen and the tissue wall at a plurality of different locations adjacent to the incision, said first lumen of said guide member being positioned relative to said carrier member such that at least a distal portion of said needle is positionable adjacent said distal member, wherein the suture material is threadable through and into the tissue wall at a first of said locations and through and back out of the tissue wall at a second of said locations.

2. An assembly, as claimed in claim 1, wherein said needle defines a first opening through the tissue wall at said first location and, upon rotation of said guide member about said carrier member, defines a second opening through the tissue wall at said second location.

3. An assembly, as claimed in claim 2, wherein said guide member has said first lumen extending therethrough for receiving and guiding said needle through the tissue wall at said first and second locations and a second lumen for receiving the suture material from one of said first and second locations.

4. An assembly, as claimed in claim 1, wherein one of said needle and a first tubular member is distally insertable through the tissue wall at said first location for providing access through the tissue wall for the suture material, and one of said needle and a second tubular member is distally insertable through the tissue wall at said second location for providing exit through the tissue wall for the suture material.

5. An assembly, as claimed in claim 1, wherein said said needle is movable axially relative to said guide member.

6. An assembly, as claimed in claim 5, wherein said needle includes a handle to axially move said needle relative to said guide member.

7. An assembly, as claimed in claim 1, wherein said guide member is movable axially relative to said carrier member.

8. An assembly, as claimed in claim 1, wherein said guide member includes a distal end portion and said distal member includes a proximal end portion, wherein said distal end portion of said guide member is engageable with said proximal portion of said distal member to define a suture pathway therebetween.

9. An assembly, as claimed in claim 8, wherein said distal end portion of said guide member comprises a male end portion and said proximal end of said distal member comprises a female end portion, wherein said male end portion is selectively insertable through the incision to engage the female end portion of said distal member to define said suture pathway therebetween.

10. An assembly, as claimed in claim 8, wherein said proximal end portion of said distal member and said distal end portion of said guide member are tapered to frictionally engage each other.

11. An assembly, as claimed in claim 8, wherein said distal member further comprises:
   a recess therein to guide the suture material along said suture pathway between said first and second locations in the tissue wall.

12. An assembly, as claimed in claim 1, further comprising:
   an aligning means, positioned on said guide member and one of said carrier member and said distal member, for aligning said needle at a plurality of predetermined positions.

13. An assembly, as claimed in claim 12, wherein a first of said predetermined positions corresponds to said first location in the tissue wall, and a second of said predetermined positions corresponds to said second location in the tissue wall.

14. An assembly, as claimed in claim 12, wherein said aligning means indicates angular rotation of said guide member relative to said carrier member.

15. An assembly, as claimed in claim 12, wherein said aligning means releasably stops further relative movement between said guide member and said distal member.

16. An assembly, as claimed in claim 15, wherein said aligning means comprises first and second stop members, said first stop member being positioned on said guide member and said stop member being positioned on said distal member.

17. An assembly, as claimed in claim 1, wherein said carrier member is tubular, said assembly further comprising:
   a guidewire positionable through said carrier member for introduction of a medical device.

18. A method for use in inserting a suture in a tissue wall of a patient comprising the steps of:
   positioning a portion of a suture insertion assembly through an incision in the tissue wall, the suture insertion assembly comprising a needle guiding means having at least a first lumen extending therethrough and a single needle received within the first lumen;
   defining a first suture access through the tissue wall at a first location with the single needle;
   rotating the needle guiding means relative to the incision in the tissue wall; and
   defining a second suture access through the tissue wall at a second location with the single needle.

19. A method, as claimed in claim 18, wherein the step of defining the first suture access and the second suture access further comprises the steps of:
   advancing the single needle distally through the tissue wall at the first location; and
   advancing the single needle distally through the tissue wall at the second location.

20. A method, as claimed in claim 19, wherein the step of defining the second suture access includes withdrawing the single needle from the tissue wall at the first location after said advancing the single needle through the tissue wall at the first location step and prior to said rotating step.

21. A method, as claimed in claim 18, wherein the suture insertion assembly further comprises a distal member, wherein said step of positioning the suture insertion assembly comprises the steps of:
   inserting at least a portion of the distal member into the incision; and
   engaging the needle guide means and the distal member to define a suture pathway therebetween, said method further comprising the step of:
   threading a suture material through the suture pathway between the first and second locations in the tissue wall.

22. A method, as claimed in claim 21, further comprising the steps of:
   disengaging the needle guide means and the distal member to proximally open the suture pathway; and
   grasping a first and a second portion of the suture material proximal to the first and second locations in the tissue wall to test the position of the suture in the tissue wall.

23. A method, as claimed in claim 22, further comprising the step of:
   suturing the incision by tying the first and second portions of the suture material to close the incision in the tissue wall.

24. An assembly for use in suturing an incision in a tissue wall of a patient with a suture material, said assembly comprising:
   a first elongated tubular member having a hollow portion and at least one opening through a side wall adjacent to said hollow portion, said first elongated member being positionable through the incision with said at least one opening being positioned distal to the tissue wall; and
   means, positionable adjacent to said first elongated member, for inserting a suture material through the tissue wall adjacent to the incision and through said at least one opening while said first elongated member is positioned through the incision.

25. An assembly, as claimed in claim 24, wherein said means for inserting comprises:
   a second elongated member positioned about said first elongated member and having at least one access hole therethrough for receiving suture material.

26. An assembly, as claimed in claim 25, wherein said second elongated member further comprises:
   an expandable portion selectably expandable from a retracted diameter to an expanded diameter larger than said retracted diameter to create a cavity between said first and second elongated members, said cavity being aligned with said at least one opening of said first elongated member.

27. An assembly, as claimed in claim 26, wherein:

distal movement of a second proximal end of said second elongated member relative to a first proximal end of said first elongated member results in expansion of said expandable portion to said expanded diameter.

28. An assembly, as claimed in claim 27, wherein:

a second distal end of said second elongated member is secured to a first distal end of said first elongated member and said second proximal end is slidable relative to said first proximal end, and wherein said second elongated member includes longitudinal slits through said expandable portion, whereby distal movement of said second proximal end relative to said first proximal end results in expansion of said expandable portion to form wing portions defining said cavity.

29. An assembly, as claimed in claim 26, wherein:

said access hole is positioned in a proximal part of said expandable portion.

30. An assembly, as claimed in claim 26, wherein:

said access hole is misaligned with said opening in said first elongated member when said expandable portion is in said retracted diameter.

31. An assembly, as claimed in claim 26, wherein:

said access hole, said cavity and said opening define an access path from an exterior of said assembly to said hollow portion when said expandable portion is in said expanded diameter.

32. An assembly, as claimed in claim 25, wherein said means for inserting comprises:

at least one needle insertable through the tissue wall and through said access hole in said second elongated member.

33. An assembly, as claimed in claim 32, wherein said means for inserting further comprises:

a third member positioned about said second elongated member and having at least one lumen extending therethrough for receiving and guiding said needle toward said access hole.

34. An assembly, as claimed in claim 33, wherein said third member is movable axially relative to said second elongated member.

35. An assembly, as claimed in claim 32, wherein said needle is a hollow needle, wherein said suture material includes a guide tip integral therewith, and wherein said means for inserting comprises:

a cannula for introducing said guide tip through said at least one hollow needle and through said at least one opening.

36. An assembly, as claimed in claim 32, further comprising:

means, interconnected with said needle, for rotationally orienting said needle relative to said first elongated member.

37. An assembly, as claimed in claim 36, wherein said means for rotationally orienting comprises:

a stop member attached to a proximal end of said needle.

38. An assembly, as claimed in claim 24, further comprising:

means, positionable within said hollow portion of said first elongated member, for engaging the suture material within said hollow portion, whereby removal of said engaging member from said hollow portion results in withdrawal of the suture material through the incision.

39. An assembly, as claimed in claim 24, further comprising:

means, positionable within said hollow portion of said first elongated member, for securing the suture material within said hollow portion, whereby removal of said first elongated member from said incision results in withdrawal of the suture material through the incision.

40. An assembly, as claimed in claim 39, wherein said means for securing comprises:

a fourth member slidably positionable within said hollow portion, whereby said fourth member is slidable toward said at least one opening to restrict the suture material between said fourth member and said sidewall of said first elongated member to thereby secure the suture material within said hollow portion.

41. An assembly, as claimed in claim 39, wherein said means for securing comprises:

an expandable member positionable within said hollow portion, whereby said expandable member is expandable to secure the suture material within said hollow portion.

42. An assembly, as claimed in claim 24, wherein said at least one opening is spaced from a distal tip of said first elongated member.

43. A method for use in suturing an incision in a tissue wall of a patient with a suture material, said method comprising the steps of:

positioning an apparatus through the incision, the apparatus comprising a first elongated member having a hollow portion and an opening through a side wall adjacent the hollow portion, the opening being positioned distal to the tissue wall;

inserting the suture material through the tissue wall and through the opening in the side wall while the first elongated member is positioned through the incision; and withdrawing the suture material through the incision.

44. A method, as claimed in claim 43, wherein the apparatus further comprises a second elongated member positioned about the first elongated member and including an expandable portion having an access hole therethrough, and wherein said step of inserting the suture material comprises:

expanding the expandable portion of the second elongated member from a retracted diameter to an expanded diameter larger than the retracted diameter to create a cavity between the first and second elongated members, the cavity being aligned with the opening of the first elongated member.

45. A method, as claimed in claim 44, wherein a second distal end of the second elongated member is secured to a first distal end of the first elongated member and a second proximal end of the second elongated member is slidable relative to a first proximal end of the first elongated member, and wherein the second elongated member includes longitudinal slits through the expandable portion, and wherein said step of expanding an expandable portion comprises:

sliding the second proximal end in a distal direction relative to the first proximal end to cause expansion of the expandable portion to form wing portions defining the cavity.

46. A method, as claimed in claim 44, wherein said step of inserting the suture material further comprises:

inserting a needle through the tissue wall and through the access hole in the second elongated member.

47. A method, as claimed in claim 46, wherein said step of inserting a needle further comprises:

inserting the needle through a lumen in a third member positioned about the second elongated member and continuing said inserting step until the needle passes through the tissue wall and through the access hole in the second elongated member.

48. A method, as claimed in claim 46, wherein the needle is a hollow needle, wherein said suture material includes a guide tip, and wherein said step of introducing the suture material comprises:

pushing the guide tip through the needle with a cannula until the guide tip is forced through the opening and into the cavity.

49. A method, as claimed in claim 43, wherein said step of withdrawing the suture material through the incision comprises:

removing the first elongated member from the incision.

50. A method, as claimed in claim 49, further comprising, before said removing step, the step of:

securing the suture material within the hollow portion.

51. A method, as claimed in claim 50, wherein said step of securing the suture material comprises:

sliding a fourth member, slidably positioned within the interior of the first elongated member, toward the opening to secure the suture material within the hollow portion.

52. A method, as claimed in claim 50, wherein said step of securing the suture material comprises:

expanding an expandable member, appropriately positioned within the interior of the first elongated member, to secure the suture material within the hollow portion.

53. A method, as claimed in claim 43, wherein said step of withdrawing the suture material through the incision comprises:

engaging the suture material within the hollow portion with an engaging member; and pulling the engaging member proximally relative to the first elongated member to withdraw the suture material through the incision.

54. An catheter introducer capable of assisting in suturing an incision in an arterial wall of a patient, said assembly comprising:

a first elongated hollow member having a sidewall and at least one opening through said sidewall, said first elongated member being positionable through the incision with said opening inside the arterial wall;

a second elongated member positioned about said first elongated member and including an expandable portion selectably expandable from a retracted diameter to an expanded diameter larger than said retracted diameter to create a cavity between said first and second elongated members, said cavity being aligned with said at least one opening, and said expandable portion including an access hole therethrough;

a third member positioned about said second elongated member and having at least one lumen extending therethrough in alignment with said cavity;

suture material; and a needle insertable into said lumen of said third member, through the arterial wall, and through the access hole in said expandable portion to provide a pathway for introduction of suture material into said first elongated member via said at least one opening, whereby withdrawal of the assembly from the incision results in the suture material being withdrawn through the incision.

55. An assembly, as claimed in claim 54, wherein said suture material includes a guide tip integral therewith, and wherein said assembly further comprises:

a cannula for introducing said guide tip through said at least one needle, whereby the guide tip may be inserted into said cavity and through said at least one opening into said hollow portion.

56. An assembly, as claimed in claim 54, wherein said suture material comprises two end portions, each being of a different color than the other.

57. An assembly, as claimed in claim 54, further comprising:

a fourth member slidably positioned within said interior of said first elongated member, whereby said fourth member is slidable toward said at least one opening to restrict the suture material between said fourth member and said sidewall of said first elongated member to secure the suture material within said hollow portion when said first elongated member is withdrawn from the incision.

58. An assembly for use in suturing an incision in a tissue wall of a patient with a suture material, said assembly comprising:

an elongated member positionable through the incision;

an expandable member positioned about said elongated member, said expandable member being selectably expandable from a retracted diameter to an expanded diameter larger than said retracted diameter to create a cavity between said elongated member and said expandable member; and means, positionable adjacent to said elongated member, for inserting a suture material through the tissue wall and into said cavity while said elongated member is positioned through the incision, said inserting means comprising at least one needle insertable through the tissue wall and through an access hole in said expandable member and an aligning member positioned about said elongated member and having at least one lumen extending therethrough for receiving and guiding said needle toward said access hole.

59. An assembly, as claimed in claim 58, wherein distal movement of a second proximal end of said expandable member relative to a first proximal end of said elongated member results in expansion of said expandable member to said expanded diameter.

60. An assembly, as claimed in claim 59, wherein a second distal end of said expandable member is secured to a first distal end of said elongated member and said second proximal end is slidable relative to said first proximal end, and wherein said expandable member includes longitudinal slits through an expandable portion thereof, whereby distal movement of said second proximal end relative to said first proximal end results in expansion of said expandable portion to form wing portions defining said cavity.

61. An assembly, as claimed in claim 58, wherein said expandable member comprises at least one said access hole positioned through a proximal part of said expandable portion.

62. An assembly, as claimed in claim 58, wherein said aligning member is movable axially relative to said elongated member.

63. An assembly, as claimed in claim 58, wherein said needle is a hollow needle, wherein said suture material includes a guide tip integral therewith, and wherein said means for inserting further comprises:

a cannula for introducing said guide tip through said at least one hollow needle and into said cavity.

64. An assembly, as claimed in claim 58, wherein said elongated member comprises a hollow portion and at least one opening through a side wall adjacent to said hollow portion, whereby said first elongated member is positionable through the incision with said at least one opening positioned distal to the tissue wall.

* * * * *